US012203882B2

United States Patent
Yu et al.

(10) Patent No.: US 12,203,882 B2
(45) Date of Patent: Jan. 21, 2025

(54) DETECTION OF PHARMACEUTICAL PRODUCT FREEZING HISTORY USING WATER PROTON NMR

(71) Applicants: Yihua Bruce Yu, Ellicott City, MD (US); Marc B. Taraban, North Potomac, MD (US); Katharine T. Briggs, Germantown, MD (US)

(72) Inventors: Yihua Bruce Yu, Ellicott City, MD (US); Marc B. Taraban, North Potomac, MD (US); Katharine T. Briggs, Germantown, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 138 days.

(21) Appl. No.: 17/436,169

(22) PCT Filed: Mar. 11, 2020

(86) PCT No.: PCT/US2020/021983
§ 371 (c)(1),
(2) Date: Sep. 3, 2021

(87) PCT Pub. No.: WO2020/185828
PCT Pub. Date: Sep. 17, 2020

(65) Prior Publication Data
US 2022/0163468 A1    May 26, 2022

Related U.S. Application Data

(60) Provisional application No. 62/816,436, filed on Mar. 11, 2019.

(51) Int. Cl.
*G01N 24/08* (2006.01)
*G01N 33/15* (2006.01)

(52) U.S. Cl.
CPC ............. *G01N 24/08* (2013.01); *G01N 33/15* (2013.01)

(58) Field of Classification Search
CPC ...... G01N 24/08; G01N 24/082; G01N 33/15; G01N 24/085; G01R 33/448
See application file for complete search history.

(56) References Cited

U.S. PATENT DOCUMENTS 6,307,372 B1 *  10/2001  Sugarman ............. G01R 33/44
                                                           422/67
8,314,618 B2    11/2012  Bieri et al.
(Continued)

FOREIGN PATENT DOCUMENTS

CN        103384724 B  * 11/2017  ............ B82Y 25/00
WO   WO 2017/210226 A1    12/2017
(Continued)

OTHER PUBLICATIONS

Pasquale, A., S. Preiss, F. Silva, and N. Garçon. 2015. Vaccine Adjuvants: from 1920 to 2015 and Beyond. Vaccines. 3: 320-343.
(Continued)

*Primary Examiner* — Jay Patidar
(74) *Attorney, Agent, or Firm* — Casimir Jones, SC; Tristan A. Fuierer

(57) ABSTRACT

A method of using the relaxation rate ($R_1$ and/or $R_2$) of solvent NMR signal to invasively or noninvasively assess whether vaccines and other aqueous-based pharmaceutical products have been frozen during transport and/or storage.

20 Claims, 9 Drawing Sheets

(56) References Cited

U.S. PATENT DOCUMENTS

| | | |
|---|---|---|
| 8,854,038 B2 | 10/2014 | Hernando et al. |
| 10,267,754 B2 | 4/2019 | Yu et al. |
| 10,514,347 B2 | 12/2019 | Yu et al. |
| 10,724,974 B2 | 7/2020 | Yu et al. |
| 11,119,061 B2 | 9/2021 | Yu et al. |
| 2004/0090231 A1 | 5/2004 | Augustine et al. |
| 2006/0228369 A1* | 10/2006 | Chen ............ A61K 39/39 424/184.1 |
| 2006/0269965 A1 | 11/2006 | Josephson |
| 2007/0116602 A1 | 5/2007 | Lee |
| 2007/0152666 A1* | 7/2007 | Thesen ............ G01N 24/08 324/306 |
| 2010/0072994 A1 | 3/2010 | Lee et al. |
| 2012/0100546 A1 | 4/2012 | Lowery et al. |
| 2012/0164644 A1 | 6/2012 | Neely et al. |
| 2013/0244238 A1 | 9/2013 | Neely et al. |
| 2013/0265054 A1 | 10/2013 | Lowery, Jr. |
| 2016/0047761 A1 | 2/2016 | Yu et al. |
| 2018/0113141 A1 | 4/2018 | Lowery, Jr. |
| 2020/0110046 A1 | 4/2020 | Yu et al. |

FOREIGN PATENT DOCUMENTS

| | | |
|---|---|---|
| WO | WO 2018/102681 A1 | 6/2018 |
| WO | 2021/127309 | 6/2021 |

OTHER PUBLICATIONS

Gupta, R.K., and E.R. Bradford Relyveld, Edgar, and Siber, George R. 1995. Adjuvant Properties of Aluminum and Calcium Compounds. In: Powell MF, MJ Newman, editors. Vaccine Design: The Subunit and Adjuvant Approach. New York, NY: Plenum Press. pp. 229-248.

Hem, S.L., and J.L. White. 1995. Structure and Properties of Aluminum-Containing Adjuvants. In: Powell MF, MJ Newman, editors. Vaccine Design: The Subunit and Adjuvant Approach. New York, NY: Plenum Press. pp. 249-276.

Baylor, N.W., W. Egan, and P. Richman. 2002. Aluminum salts in vaccines—US perspective. Vaccine, 20(Suppl. 3), S18-S23.

Exley, C.; Siesjö, P.; Eriksson, H. The immunobiology of aluminium adjuvants: How they really work? Trends Immunol. 2010, 31, 103-109.

Farrell, C. Analytical control strategies for aluminum adjuvants. WCBP 2014, https://www.casss.org/resource/resmgr/WCBP_Speaker_Slides/2014_WCBP_Chris_Farrell.pdf.

Kumru, O.S., S.B. Joshi, D.E. Smith, C.R. Middaugh, T. Prusik, and D.B. Volkin. 2014. Vaccine instability in the cold chain: Mechanisms, analysis and formulation strategies. Biologicals. 42: 237-259.

Guo, J.; Lewis, L. M.; Billones, H.; Torres, E.; Kolhe, P. The effect of shipping stresses on vaccine re-dispersion time. J. Pharm. Sci. 2016, 105, 2009-2013.

Gupta, R. K. Aluminum compounds as vaccine adjuvants. Adv. Drug Deliv. Rev. 1998, 32, 155-172.

Dumpa, N., K. Goel, Y. Guo, H. McFall, A.R. Pillai, A. Shukla, M.A. Repka, and S.N. Murthy. 2019. Stability of Vaccines. AAPS PharmSciTech. 20: 42.

HogenEsch, H.; O'Hagan, D. T.; Fox, C. B. Optimizing the utilization of aluminum adjuvants in vaccines: you might just get what you want. NPJ Vaccines 2018, 3, 51.

Østergaard, E., P.L. Frandsen, and E. Sandberg. 2015. Determination of freeze damage on HPV vaccines by use of low cytometry. Biologicals. 43: 266-273,.

Chesko, J., T. Vedvick, and S. Reed. 2013. Development of Biophysical Assays to Better Understand Adjuvanted Vaccine Formulation Potency and Stability, In: Novel immune potentiators and delivery technologies for next generation vaccines, M. Singh Ed., Springer, New York, 107-118.

Kurztowski, W.; Kartoğlu, Ü.; Staniszewska, M.; Górska, P.; Krause, A.; Wysocki, M. J. Structural damages in adsorbed vaccines affected by freezing. Biologicals 2013, 41, 71-76.

Kurztowski, W.; Kartoğlu, Ü.; Górska, P.; Glówka, M.; Woźnica, K.; Zasada, A. A.; Szczepańska, G.; Trykawski, G.; Gniadek, M.; Donten, M. Physical and chemical changes in AlhydrogelTM damaged by freezing. Vaccine 2018, 36, 6902-6910.

Langford, A.; Horwitz, T.; Adu-Gyamfi, E.; Wiley, C.; Holding, E.; Zimmermann, D.; Ignatius, A. A.; Ohtake, S. Impact of formulation and suspension properties on redispersion of aluminum-adjuvanted vaccines. J. Pharm. Sci. 2020, 109, 1460-1466, Abstract Only.

Lewis, L. M.; Guo, J.; Torres, E.; Wang, J.; Billones, H.; Kolhe, P.; Young, A. L.; Bates, D.; Parker, A.; Rigby-Singleton, S. Ex situ and in situ characterization of vaccine suspensions in pre-filled syringes. J. Pharm. Sci. 2017, 106, 2163-2167.

Meiboom, S.; Gill, D. Modified spin-echo method for measuring nuclear relaxation times. Rev. Sci. Instrum. 1958, 29, 688-691.

Muthurania, K.; Ignatius, A. A.; Jin, Z.; Williams, J.; Ohtake, S. Investigation of the sedimentation behavior of aluminum phosphate: Influence of pH, ionic strength, and model antigens. J. Pharm. Sci. 2015, 104, 3770-3778.

Metz, B., G. van den Dobbelsteen, C. van Els, J. van der Gun, L. Levels, L. van der Pol, N. Rots, and G. Kersten. 2009. Quality-control issues and approaches in vaccine development. Expert Rev. Vaccines. 8: 227-238.

Reed, S. G.; Orr, M. T.; Fox, C. B. Key roles of adjuvants in modern vaccines. Nat. Med. 2013, 19, 1597-1608.

Salnikova, M. S.; Davis, H.; Mensch, C.; Celano, L.; Thiriot, D. S. Influence of formulation pH and suspension state on freezing-induced agglomeration of aluminum adjuvants. J. Pharm. Sci. 2012, 101, 1050-1062.

Shardlow, E.; Mold, M.; Exley, C. From stock bottle to vaccine: Elucidating the particle size distributions of aluminum adjuvants using dynamic light scattering. Front. Chem. 2017, 4, 48.

Taraban, M. B.; Fox, C. B.; Yu, Y. B. Assessing aluminum vaccine adjuvant filling, sedimentation, and resuspension in sealed vials using water proton NMR. Am. Pharm. Rev. 2019, 22, 70-73.

Vecchi, S.; Bufali, S.; Skribinski, D. A. G.; O'Hagan, D. T.; Singh, M. Aluminum adjuvant dose guidelines in vaccine formulation for preclinical evaluations. J. Pharm. Sci. 2012, 101, 17-20.

Briggs, K.T., Taraban, M.B., Yu, Y.B. (2018) Water proton NMR detection of amide hydrolysis and diglycine dimerization. Chem. Comm. 54, 7003-7006.

Clapp, T., M.W. Munks, R. Trivedi, U.B. Kompella, and L.J. Braun. 2014. Freeze-thaw stress of Alhydrogel® alone is sufficient to reduce the immunogenicity of a recombinant hepatitis B vaccine containing native antigen. Vaccine. 32: 3765-3771.

World Health Organization 2006, WHO/IVB/06.10.

Yu, Y.B., Feng, Y., Taraban, M.B. (2017) Water proton NMR for noninvasive chemical analysis and drug product inspection. Am. Pharmaceut. Rev. 20, 34-39.

Taraban, M.B., Truong, H.C., Feng, Y., Jouravleva, E.V., Anisimov, M.A., Yu, Y.B., (2015) Water Proton NMR for In Situ Detection of Insulin Aggregates, J. Pharm. Sci., 104, 4132-4141.

Taraban, M.B., DePaz, R.A., Lobo, B., Yu, Y.B. (2017) Water proton NMR: a tool for protein aggregation characterization. Anal. Chem. 89, 5494-5502.

Taraban, M.B., Truong, H., Ilavsky, J., DePaz, R.A., Lobo, B., Yu, Y.B. (2017) Non-invasive detection of nanoparticle clustering by water proton NMR. Transl. Mater. Res. 4, 025002.

Taraban, M.B., Briggs, K.T., Merkel, P., Yu, Y.B., Flow Water Proton NMR: In-Line Process Analytical Technology for Continuous Biomanufacturing (2019) Anal. Chem. 91, 13538-13546.

Taraban, M et al.; "Water Flow-NMR-A Prospective Contact-Free In-Line Analytical Tool for Continuous Biomanufacturing," Mar. 3, 2019, PANIC 2019 conference (Practical Applications of NMR in Industry Conference), Poster.

Baroni, et al.; "Relaxometric Characterization of Balsamic Vinegar," meeting abstract 6th Conference on Field Cycling NMR Relaxometry Turin (Italy) Jun. 4, 2009.

Bloembergen, N. et al.; "Relaxation Effects in Nuclear Magnetic Resonance absorption," Phys. Rev. 1948, 73, 679-712.

(56) References Cited

OTHER PUBLICATIONS

Feng, Y., Taraban, M.B., Yu, Y.B. (2011) Linear dependency of NMR relaxation rates on shear modulus in hydrogels. Soft Matter, 7, 9890-9893.

Feng, Y., Taraban, M.B., Yu, Y.B., (2015) Water Proton NMR—A Sensitive Probe for Solute Association, Chem. Commun., 51, 6804-6807.

Lloyd, J., and J. Cheyne. 2017. The origins of the vaccine cold chain and a glimpse of the future. Vaccine. 35: 2115-2120.

Robertson, J., L. Franzel, and D. Maire. 2017. Innovations in cold chain equipment for immunization supply chains. Vaccine. 35: 2252-2259.

World Health Organization 2005, WHO/V&B/03.18.Rev. 1.

Setia, S., H. Mainzer, M.L. Washington, G. Coil, R. Snyder, and B.G. Weniger. 2002. Frequency and causes of vaccine wastage, Vaccine. 20: 1148-1156.

CDC/NCIRD, Vaccine Storage and Handling, best practice guidance for storage and handling of vaccines, Pinkbook 2012, Chapter 5, Epidemiology and Prevention of Vaccine-Preventable Diseases, 12th Edition Second Printing Revised May 2012.

World Health Organization. 2015. Module 2: The Vaccine Cold Chain. Immunization in Practice. A Practical Guide for Health Staff: 44-46.

Pan American Health Organization, Immunization Newsletter, 2010. How to perform the "Shake Test ." vol. XXXII: 2010.

Clausi, A.L., S.A. Merkley, J.F. Carpenter, and T.W. Randolph. 2008. Inhibition of aggregation of aluminum hydroxide adjuvant during freezing and drying. J. Pharm. Sci. 97: 2049-2061.

Wolff, L., J. Flemming, R. Schmitz, K. Gröger, and C. Müller-Goymann. 2008. Protection of aluminum hydroxide during lyophilisation as an adjuvant for freeze-dried vaccines. Colloids Surfaces A Physicochem. Eng. Asp. 330: 116-126.

Dimayuga R., D. Scheifele, and A. Bell. 1995. Effects of freezing on DTP and DTP-IPV vaccines, adsorbed. Can. Commun. Dis. Rep. 21: 101-3 pmid: 7647743.

Kartoglu U., N.K. Özgüler, L.J. Wolfson, and W. Kurzatkowski. 2010. Validation of the shake test for detecting freeze damage to adsorbed vaccines. Bulletin of the World Health Organization. 88:624-631.

Metz, H., K. Mader. 2008. Benchtop-NMR and MRI—a new analytical tool in drug delivery research. Int. J. Pharm. 364: 170-178.

International Search Report for PCT/US2020/021983, mailed Jun. 10, 2020, 3 pages.

Clapp et al., Vaccines with aluminum-containing adjuvants: optimizing vaccine efficacy and thermal stability. Journal of Pharmaceutical Sciences., Aug. 25, 2010, col. 100, No. 2, pp. 388-401.

* cited by examiner

DETECTION OF PHARMACEUTICAL PRODUCT FREEZING HISTORY USING WATER PROTON NMR

CROSS-REFERENCE TO RELATED APPLICATIONS

This application is filed under the provisions of 35 U.S.C. § 371 and claims the priority of International Patent Application No. PCT/US2020/021983 filed on 11 Mar. 2020, which claims priority to U.S. Provisional Patent Application No. 62/816,436, filed on 11 Mar. 2019 and entitled "Non-invasive and Quantitative Detection of Pharmaceutical Product Freezing History Using Water Proton NMR" in the name of Yihua (Bruce) Y U et al., both of which are incorporated herein by reference in their entirety.

STATEMENT OF FEDERAL SUPPORT

This invention was made with government support under Grant No. 01FD005946 awarded by the Food and Drug Administration. The government has certain rights in the invention.

FIELD

The present invention relates to methods for quality control of pharmaceutical products, including drugs and vaccines, using solvent nuclear magnetic resonance (NMR). The methods can be used to determine whether individual pharmaceutical products have been damaged by freezing and should be removed from the distribution stream.

DESCRIPTION OF THE RELATED ART

Vaccines are critical in combating the spread of infectious diseases worldwide. Vaccines confer resistance to a particular disease by awakening the body's innate immune system through exposure to an antigen, or multiple antigens in the case of combination vaccines, specific to that disease, which in turn causes an adaptive immune system response that is protective in nature (1). In addition to antigens, vaccines often contain adjuvants, or substances that improve the immune response. Adjuvants are beneficial because they often allow the vaccine dose to be lowered. The most commonly used adjuvants are aluminum salts (1), although new adjuvants are currently being developed and licensed, such as squalene-based emulsions and virosomes. The mechanism by which antigens adsorbed onto aluminum salts enhance the immune response is still unclear, but it is proposed that they increase inflammation at the site of injection (1-3). The U.S. Food and Drug Administration (FDA) regulations allow for a maximum of 0.85 mg of Al(III) in the form of aluminum salt per dose to prevent serious irritation at the injection site, but vaccines containing aluminum-adjuvants, first introduced in 1926, have a long history of safety (4).

Despite their widespread use and critical importance, vaccines, in particular aluminum-adjuvanted vaccines, are thermally unstable outside their recommended storage temperature, either when they are exposed to lower or higher temperatures, or both (5, 6). Their instability is due to their susceptibility to degradation, agglomeration/aggregation, or other structural molecular changes (7). These molecular changes can be observed by several of the same techniques that are used in characterizing the vaccine components during development (e.g., scanning electron microscopy, flow cytometry, dynamic light scattering, microflow imaging, classical spectroscopic methods); however, the vials that are tested are compromised and therefore are no longer usable as vaccines (7-10). Freeze-induced damage to aluminum-adjuvanted vaccines leads to a loss of vaccine potency through a weakened immune response (6, 11). Even a slight potency loss could render a vaccine ineffective in its protective capacity against an infectious disease. For this reason, the temperature of a vaccine during its transportation and shipment, as well as storage prior to use, is carefully monitored and maintained. The World Health Organization presently recommends that all vaccines are stored at 2° C. to 8° C. (12).

The supply chain of vaccines and other pharmaceutical products that need to be kept refrigerated is also known as the "cold-chain" or "temperature controlled." In the last decade, the cold-chain has improved through the use of new technology, such as temperature-sensitive vial container monitors, and new equipment, such as high performance carriers, solar direct-drive refrigerators, and long term cold-boxes (13, 14). When temperature monitoring devices or regular recording protocols observe that a temperature excursion has occurred, procedures are in place for trained personnel to take appropriate action. Despite this, the WHO has reported over 50% vaccine wastage worldwide because of frozen or suspected to be frozen vaccines, and in particular cold-chain lapses, being one of the major reasons for wastage (15, 16).

The first line of freezing detection is visual observation of ice. In actual cold chain management, if ice is visually observed in vials, then those vials should not be used. There is no ambiguity in such a case. Ambiguity arises when the temperature monitoring device records/reports exposure to subzero temperature, but no ice is seen in any vial. The Center for Disease Control (CDC) issued guidance advising that a batch of vaccines that may have experienced lower than recommended temperatures at any point during shipping and distribution should be separated from other vaccines and labeled "do NOT use." Personnel are advised to wait for further directions from the distributer or manufacturer (17). Outside the U.S., the World Health Organization (WHO) recommends that the batch in question be tested using "the Shake Test," a qualitative test whereby a few vials of the batch suspected to have been frozen are pulled and checked to infer whether the whole batch has been frozen. A trained person removes the vaccine labels from the pulled vials and visually compares an intentionally frozen (and then thawed) vial with a pulled vial (i.e., a vial suspected to have been unintentionally frozen). Upon shaking both vials, the frozen vaccine will have characteristic flakes that settle quicker than non-frozen vaccines, which appear more cloudy (18, 19). The benefit of "the Shake Test" is that it does not require any technology and can be performed "in the field" because it is based on freezing-induced physical changes (7, 20, 21). Disadvantageously, the "Shake Test" requires a trained human observer, the removal of the vaccine label, requires that non-compromised vials have to be frozen, and takes approximately 5-45 minutes (22). It has been said that "Mlle key to deciding whether a shake test has passed or failed is the patience of the observer" (23).

There is a need for a fast and reliable technique which can be used for quality control in vaccine transport and storage to determine if the sealed vaccines in the distribution chain have been frozen. Towards that end, the present invention relates to a method of using the transverse relaxation rate of the solvent NMR signal, e.g., $R_2(^1H_2O)$, to determine whether the contents of a filled and sealed pharmaceutical product container have been frozen. Advantageously, the method described herein is easy to use, can be used noninvasively, provides nearly immediate results, and is highly-sensitive.

SUMMARY

The present invention generally relates to a method of using NMR relaxation rates, specifically the transverse relaxation rate constant $R_2$ of water to determine if a pharmaceutical product such as a vaccine or a drug has experienced freeze-induced damage during transportation and storage.

In one aspect, a method of determining if a vaccine or aqueous-based pharmaceutical product has experienced freeze-induced damage is described, said method comprising: measuring the transverse relaxation rate of solvent $R_{2,m}$ in the vaccine or aqueous-based pharmaceutical product; and determining if the vaccine or aqueous-based pharmaceutical product has been frozen by comparing the measured $R_{2,m}$ to a reference transverse relaxation rate of solvent $R_{2,r}$, wherein the reference $R_{2,r}$ represents an acceptable range for non-frozen vaccine or non-frozen aqueous-based pharmaceutical product, wherein when the measured $R_{2,m}$ is inside the reference $R_{2,r}$ range, the vaccine or aqueous-based pharmaceutical product has not experienced freeze-induced damage.

In another aspect, a method of determining if a vaccine or aqueous-based pharmaceutical product has experienced freeze-induced damage is described, said method comprising: measuring the longitudinal relaxation rate of solvent $R_{1,m}$ in the vaccine or aqueous-based pharmaceutical product; and determining if the vaccine or aqueous-based pharmaceutical product has been frozen by comparing the measured $R_{1,m}$ to a reference longitudinal relaxation rate of solvent $R_{1,r}$, wherein the reference $R_{1,r}$ represents an acceptable range for non-frozen vaccine or non-frozen aqueous-based pharmaceutical product, wherein when the measured $R_{1,m}$ is inside the reference $R_{1,r}$ range, the vaccine or aqueous-based pharmaceutical product has not experienced freeze-induced damage.

Other aspects, features and advantages of the invention will be more fully apparent from the ensuing disclosure and appended claims.

7B illustrates $R_2(^1H_2O)$ of ALHYDROGEL unstressed vials 1-3 and freeze/thaw vials 4-6 measured at 25° C. after the first (light triangle), second (medium triangle), and third (dark triangle) freeze-thaw cycle in the thawed liquid suspension state. Initial $R_2(^1H_2O)$ measurements of vials 1-6

(pre-freeze stress) are shown as averages in the suspended adjuvant (solid line) and settled adjuvant (dashed line) states.

Figure 8B:
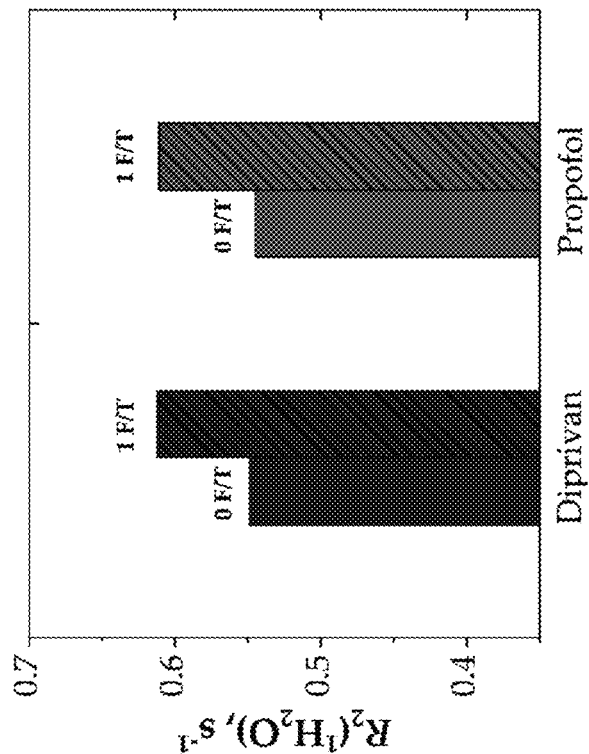
Figure 8A:
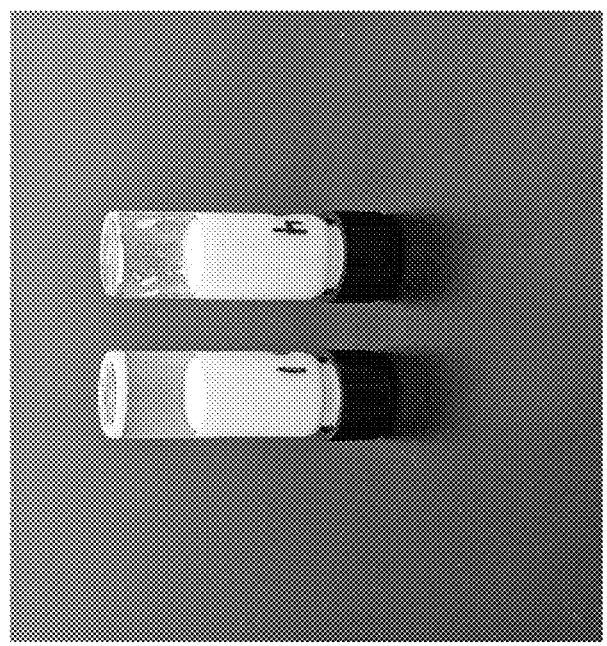

FIG. 8A is an image of the visual appearance of vials with 0 freeze-thaw (F/T) (left) relative to vials containing the same emulsion drug with 1 F/T (right).

FIG. 8B illustrates the $R_2(^1H_2O)$ for both DIPRIVAN and PROPOFOL with 0 F/T and 1 F/T.

Figure 9A:

FIG. 9A is a photo of an unopened vial of DIPRIVAN.

Figure 9B:
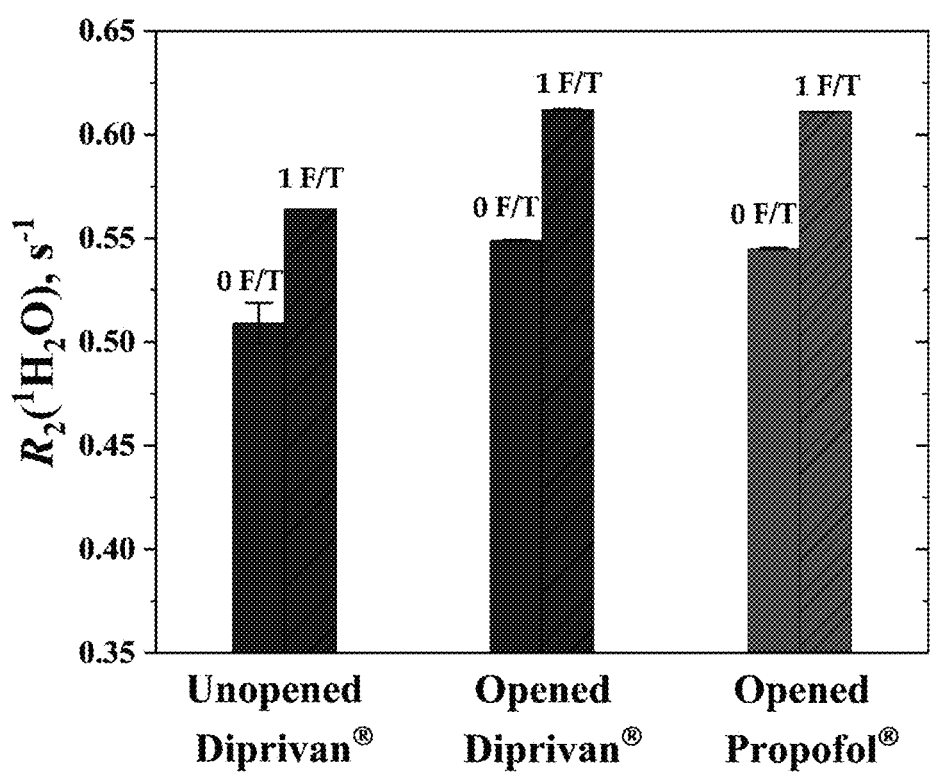

FIG. 9B illustrates $R_2(^1H_2O)$ of unopened DIPRIVAN, opened DIPRIVAN, and opened PROPOFOL after 0 F/T and 1 F/T.

DETAILED DESCRIPTION, AND PREFERRED EMBODIMENTS THEREOF

The present invention generally relates to a method of using NMR relaxation times or rates (longitudinal and transverse relaxation rate constants, $R_1$ and $R_2$, respectively) of solvent molecules, e.g., water, to determine if a pharmaceutical product such as a vaccine or a drug has experienced freeze-induced damage during transportation and storage. If damage is determined, the pharmaceutical product can be removed from the distribution chain to ensure it isn't administered to a patient.

As defined herein, a "pharmaceutical product" can include vaccines and drugs, including biologics and small molecules (i.e., non-biologics), in an aqueous medium. The pharmaceutical products can further comprise at least one adjuvant, at least one surfactant, at least one water-soluble organic solvent, at least one dispersant, at least one biocide, at least one buffering agent, at least one pH adjusting agent (e.g., acids and/or bases), at least one peptide, at least one polypeptide, at least one protein, at least one antibody or fragment thereof, at least one nucleic acid, at least one oil, or any combination thereof, as readily determined by the person skilled in the art. In one embodiment, the pharmaceutical product comprises an emulsion. Notably, the methods described herein are preferentially used with pharmaceutical products that include in the instructions that the product should not be frozen prior to administration to a patient. It should be appreciated that a patient includes any human or other mammal, reptile, bird, fish, or amphibian.

For the purposes of the present application, reference will be made to vaccines comprising aluminum adjuvants, and emulsion drugs, however the method is not limited to vaccines and emulsion drugs and is intended to be extended to any pharmaceutical product as defined herein.

The prior art methods of determining if a vaccine has been exposed to freezing conditions, e.g., visual inspection and/or the Shake Test, are difficult and often impractical. To visually observe coloration, density, or sedimentation variations in a small vial containing volumes of 0.5 mL (e.g., most children's vaccines) and 1 mL (e.g., most adult vaccines) is not objectively reasonable, even when the label has been removed.

Further, vaccines are known to be homogenous, turbid, white suspensions when shaken before use. Package inserts for vaccines typically include instructions to visually inspect the vials containing the vaccines for particulate matter and discoloration prior to administration, whenever solution and container permit. It is possible to look from the bottom of the vial, but in the absence of an obviously large particle or discoloration, this visual observation at the point of administration would be very difficult to detect anything more than enormous changes or irregularities.

The method described herein is a reliable and simple method to assess whether vaccines and other pharmaceutical products were frozen during transportation and/or storage of same (i.e., while in the cold-chain). The method enables the assessment of the vaccines and other pharmaceutical products, formulated as aqueous suspensions, without the requirement of opening the vial or product container, without peeling off the label on the vial, and without waiting for a sedimentation time course. The method is quantitative and comprises measuring the nuclear spin relaxation rate constant, $R_1$ and/or $R_2$, of solvent, e.g., water, as a quality control parameter. It is known that freeze-induced damage to vaccines leads to a loss of vaccine potency and even a slight potency loss can render a vaccine ineffective in its protective capacity against an infectious disease. In the present disclosure, freeze-induced damage to the vaccines and other pharmaceutical products is evidenced by a quantitative variation (either an increase or a decrease) of the nuclear spin relaxation rate constant, $R_1$ and/or $R_2$, of solvent, e.g., water. The $R_1$ and/or $R_2$ constant of the non-frozen vaccine, or preferentially an acceptable range of $R_1$ and/or $R_2$ constants of said non-frozen vaccine, can be determined by the manufacturer. The $R_1$ and/or $R_2$ constant (or range of $R_1$ and/or $R_2$ constants) can be provided in the package insert, on the vial label, or both. Thereafter, the vaccine is released for sale and purchase and enters the "cold-chain," whereby it is transported and/or stored, and may be exposed to freezing temperatures. The $R_1$ and/or $R_2$ constant of water can be measured by the transporter or distributor or the purchaser/user before use to confirm that the vaccine has not been frozen. If the measured $R_1$ and/or $R_2$ constant (or range of $R_1$ and/or $R_2$ constants) of the vaccine is outside of the reference range provided by the manufacturer, meaning that the contents may have been frozen, the specific vial can be rejected.

Recent breakthrough developments in the instrumentation for nuclear magnetic resonance (NMR) spectroscopy and imaging have opened up opportunities to design novel analytical techniques for the nanoparticle industry. Of special importance was the introduction of commercially available, relatively inexpensive benchtop and handheld NMR and magnetic resonance imaging (MRI) instruments and relaxometers (24). Benchtop NMR instruments enable highly accurate measurements of nuclear spin relaxation times $T_1$ and $T_2$. Moreover, most of these instruments have a permanent or electronically cooled magnet with the variable bore from 10 mm to 45 mm and even larger which provides a great flexibility in the measurements of vials of various sizes.

Water proton NMR (wNMR) monitors water, which acts as a reporter for analytes dissolved in it. As a reporter, water has two tremendous advantages. First, its concentration far surpasses that of any analyte dissolved in it, by $10^3$-$10^6$ fold in most cases. This makes the $^1H_2O$ signal easily detectable by benchtop and handheld NMR instruments. Further, the solute association can be detected through the solvent NMR signal. In addition, water is "endogenous" to all biomanufacturing processes and all pharmaceutical products, including vaccines and drugs. This sets it apart from "exogenous" reporters such as fluorescent dyes or radiotracers. The high concentration of "endogenous" water make it possible for wNMR to be contact-free in situ.

The essence of wNMR is a consistency check, which makes it useful for the pharmaceutical industry, where consistency is both critical and expected. For example, as described herein, wNMR can be used to determine if the contents of the pharmaceutical, e.g., vaccine, vials have been frozen during transportation and/or storage. With the knowledge provided by the present invention, accidentally frozen pharmaceutical products can be identified with certainty, thus protecting patients from ineffective or harmful products. Additionally, since the present invention can be used non-invasively, the unnecessary waste of non-frozen pharmaceutical products in a batch exposed to freezing temperatures can be prevented.

As defined herein, the "aluminum-containing product" includes a product with nano- and micron-sized alum particles suspended in a solvent or a mixture of solvents. The aluminum-containing product can further comprise at least one surfactant, at least one water-soluble organic solvent, at least one dispersant, at least one biocide, at least one buffering agent, at least one pH adjusting agent (e.g., acids and/or bases), at least one oil, with or without antigens, or any combination thereof, as readily determined by the person skilled in the art. As is readily understood by the person skilled in the art, an aluminum-containing product includes many vaccines wherein the aluminum is present as an adjuvant.

As defined herein, a "vial" corresponds to a container, vessel, bottle, syringe, injection pen, or ampoule used to store the vaccine or pharmaceutical product, wherein the vial comprises glass, plastic, ceramic, rubber, elastomeric material, and/or anything non-magnetic metal. The vial can have a screw top, a top that is closed using a cork or plastic stopper, a crimp vial (closed with a rubber stopper and a metal cap), a flip-top or snap cap. The vial can be tubular, or have a bottle-like shape with a neck. Other types and shapes of vials used to store particles as well as caps are readily understood by the person skilled in the art. The vials can be optically transparent or not optically transparent. There is no need to peel off any label on the vial, whether the label is transparent or not.

As defined herein, a "non-destructive" measurement is defined as a measurement performed without opening the vial or otherwise accessing, harming, or altering the contents of the vial (for example by withdrawing a portion through a rubber gasket). Moreover, a non-destructive measurement means that no additives or probes or the like are added to the vial prior to the measurement of the transverse relaxation rate of water $R_2$ in the vaccine or other pharmaceutical product. Non-destructive also means that there is no need to make the vials optically transparent and no need to peel off any labels on the vials.

The pharmaceutical products will have a freezing point that varies depending on the constitution of the specific product. That said, as will be discussed, two vials in the same batch exposed to the same temperature can yield different results whereby one may freeze and one may remain unfrozen at the same temperature. It is understood by the person skilled in the art that to "freeze" means to convert a liquid into a solid as a result of exposure to temperatures below a freezing point. For the purposes of this disclosure, to have been previously "frozen" corresponds to a product having a $T_2(^1H_2O)$, $T_1(^1H_2O)$, $R_2(^1H_2O)$, or $R_1(^1H_2O)$ value that is statistically different than the non-frozen control. For the purposes of this disclosure, "experienced freeze-induced damage" is intended to mean that the product has been frozen, intentionally or accidentally. A frozen product should be discarded immediately. Unexpectedly, just because the temperature of the vaccine or pharmaceutical product was for some period of time excursed below the freezing point for the specific product does not mean that the product has been frozen.

As understood by the person skilled in the art, refrigeration temperatures are in a range from about 2° C. to about 8° C.

As defined herein, the aluminum in an aluminum-containing product comprises one or more of aluminum hydroxide, aluminum phosphate, aluminum sulfoxyphosphate, aluminum hydroxyphosphate sulfate, alum ($KAl(SO_4) \cdot 12H_2O$), as well as other known or proprietary aluminum salts that can be used as aluminum adjuvants in vaccines or in pharmaceutical products comprising aluminum.

The present inventors have surprisingly discovered that solvent NMR can be used to detect if vaccines and other pharmaceutical products in filled and sealed vials have been frozen upon exposure to freezing temperatures. The manufacturer as well as transporters, distributors, commercial end users, and researchers can use solvent NMR to inspect the vaccines and pharmaceutical products for freeze-induced damage. Advantages of low field solvent NMR includes low cost instrumentation (e.g., a benchtop, desktop, or hand-held NMR), simple and rapid data acquisition and analysis, and minimal technical expertise requirement whereby the results are readily available within <1 min. In a preferred embodiment, the method of using solvent NMR to inspect vaccines and pharmaceutical products for freeze-induced damage is non-invasive. It should be appreciated that the measurements can occur destructively as well, whereby the vial is opened, if needed. Further, the method described herein can utilize high field NMR, if needed and can be used in continuous-flow manufacturing processes. In addition, the methods described herein can be used with an originator pharmaceutical product or reference listed drug (RLD) or a follow-on version thereof.

It was discovered that once a vaccine has been frozen at least once, after thawing, the $R_2(^1H_2O)$ value can be significantly different, as much as ~50% lower, relative to a non-frozen control. Interestingly though, the method described herein also revealed that exposing a vial of vaccine to freezing temperatures (e.g., −18° C., 15+ hrs) does not necessarily lead to a frozen product. Some vaccines can be exposed to freezing temperatures and not be frozen per se, and thus there is negligible or no change in the $R_2(^1H_2O)$ value relative to a non-frozen control.

In practice, the manufacturer can provide the acceptable $R_2(^1H_2O)$ or $R_1(^1H_2O)$ range in $sec^{-1}$, e.g., a control or reference range, for the non-frozen vaccine or pharmaceutical product at refrigeration temperatures (e.g., about 2° C. to about 8° C.) and specific magnetic field strength (s) (e.g., 0.5 T). The user will then measure the $R_2(^1H_2O)$ or $R_1(^1H_2O)$ of the vaccine or pharmaceutical product at the same temperature and magnetic field strength and compare the measured $R_2(^1H_2O)$ or $R_1(^1H_2O)$ value with the manufacturer-specified acceptable range of $R_2(^1H_2O)$ or $R_1(^1H_2O)$, i.e., reference, as understood by the person skilled in the art, to determine if the vaccine or pharmaceutical product experienced freeze-induced damage.

Accordingly, in a first aspect, a method of determining if a vaccine or other aqueous-based pharmaceutical product has experienced freeze-induced damage is described, said method comprising: measuring the transverse relaxation rate of solvent $R_{2,m}$ in the vaccine or aqueous-based pharmaceutical product; and determining if the vaccine or aqueous-based pharmaceutical product has been frozen by comparing the measured $R_{2,m}$ to a reference transverse relaxation rate of solvent $R_{2,r}$, wherein the reference $R_{2,r}$ represents an acceptable range for non-frozen vaccine or aqueous-based pharmaceutical product, wherein when the measured $R_{2,m}$ is inside the reference $R_{2,r}$ range, the vaccine or aqueous-based pharmaceutical product has not experienced freeze-induced damage. In one embodiment, the pharmaceutical product comprises biologics or small molecules. In another embodiment, the vaccines or pharmaceutical products comprise at least one component selected from the group consisting of at least one adjuvant, at least one surfactant, at least one water-soluble organic solvent, at least one dispersant, at least one biocide, at least one buffering agent, at least one pH adjusting agent, at least one peptide, at least one polypeptide, at least one protein, at least one antibody or fragment thereof, at least one nucleic acid, at least one oil, and any combination thereof. The transverse relaxation rate of solvent $R_2$ can be determined using solvent NMR, preferably low field solvent NMR. Preferably, the measuring of the transverse relaxation rate of solvent $R_2$ in the vaccine or pharmaceutical product can be done non-invasively in a vial, but it should be appreciated that the measurement can be done invasively as well, as readily understood by the person skilled in the art. The reference $R_{2,r}$ range, at a specified temperature and magnetic field strength, can be measured by the manufacturer and the result listed in the package insert and/or the vial of the vaccine or pharmaceutical product. Preferably $R_{2,m}$ is measured at substantially the same temperature and magnetic field strength as $R_{2,r}$. The distributor or purchaser can then use NMR, e.g., benchtop or handheld, to measure $R_{2,m}$ at the specified temperature and magnetic field strength and compare it with the reference $R_{2,r}$ range listed in the package insert or vial before distribution or usage. If the measured $R_{2,m}$ is inside the reference $R_{2,r}$ range, the vaccine or aqueous-based pharmaceutical product has not experienced freeze-induced damage, and as such can be distributed or used.

It should be appreciated that the method of the first aspect can be based on the water proton transverse relaxation time $T_2$, instead of the rate $R_2$, as readily determined by the person skilled in the art. In other words, when water is the solvent, the manufacturer provides $T_2(^1H_2O)$ reference values for the acceptable range for non-frozen vaccine or aqueous-based pharmaceutical product and the measured $T_2(^1H_2O)$ of the vaccine or aqueous-based pharmaceutical product is compared to the $T_2(^1H_2O)$ reference values. The transverse relaxation time $T_2(=1/R_2)$ value can be extracted by fitting experimental data to Formula (1):

$$I(t)=I_0 \times \exp(-t/T_2) \quad (1)$$

where I(t) is the $^1H_2O$ signal intensity at time t, $I_0$ is the initial $^1H_2O$ signal intensity when t=0, and t is the $T_2$ delay time.

In a second aspect, a method of determining if a vaccine or other aqueous-based pharmaceutical product has experienced freeze-induced damage is described, said method comprising: measuring the longitudinal relaxation rate of solvent $R_{1,m}$ in the vaccine or aqueous-based pharmaceutical product; and determining if the vaccine or aqueous-based pharmaceutical product has been frozen by comparing the measured $R_{1,m}$ to a reference longitudinal relaxation rate of solvent $R_{1,r}$, wherein the reference $R_{1,r}$ represents an acceptable range for non-frozen vaccine or aqueous-based pharmaceutical product, wherein when the measured $R_{1,m}$ is inside the reference $R_{1,r}$ range, the vaccine or aqueous-based pharmaceutical product has not experienced freeze-induced damage. In one embodiment, the pharmaceutical product comprises biologics or small molecules. In another embodiment, the vaccines or pharmaceutical products comprise at least one component selected from the group consisting of at least one adjuvant, at least one surfactant, at least one water-soluble organic solvent, at least one dispersant, at least one biocide, at least one buffering agent, at least one pH adjusting agent, at least one peptide, at least one polypeptide, at least one protein, at least one antibody or fragment thereof, at least one nucleic acid, at least one oil, and any combination thereof. The longitudinal relaxation rate of solvent $R_1$ can be determined using solvent NMR, preferably low-field solvent NMR. Preferably, the measuring of the longitudinal relaxation rate of solvent $R_1$ in the vaccine or pharmaceutical product can be done non-invasively in a vial, but it should be appreciated that the measurement can be done invasively as well, as readily understood by the person skilled in the art. The reference $R_{1,r}$ range, at a specified temperature and magnetic field strength, can be measured by the manufacturer and the result listed in the package insert and/or the vial of the vaccine or pharmaceutical product. Preferably $R_{1,m}$ is measured at substantially the same temperature and magnetic field strength as $R_{1,r}$. The distributor or purchaser can then use NMR, e.g., benchtop or handheld, to measure $R_{1,m}$ at the specified temperature and magnetic field strength and compare it with the reference $R_{1,r}$ range listed in the package insert or vial before distribution or usage. If the measured $R_{1,m}$ is inside the reference $R_{1,r}$ range, the vaccine or aqueous-based pharmaceutical product has not experienced freeze-induced damage, and as such can be distributed or used.

It should be appreciated that the method of the second aspect can be based on the water proton longitudinal relaxation time $T_1$, instead of the rate $R_1$, as readily determined by the person skilled in the art. In other words, when water is the solvent, the manufacturer provides $T_1(^1H_2O)$ reference values for the acceptable range for non-frozen vaccine or aqueous-based pharmaceutical product and the measured $T_1(^1H_2O)$ of the vaccine or aqueous-based pharmaceutical product is compared to the $T_1(^1H_2O)$ reference values. The longitudinal relaxation time $T_1 (=1/R_1)$ can be extracted by fitting experimental data to Formula (2) if the inversion recovery pulse sequence was used:

$$I(t)=I_0 \times [1-2*\exp(-t/T_1)] \quad (2)$$

or by fitting experimental data to Formula (3) if the saturation recovery pulse sequence was used:

$$I(t)=I_0 \times [1-\exp(-t/T_1)] \quad (3)$$

where I(t) is the $^1H_2O$ signal intensity at time t, $I_0$ is the $^1H_2O$ signal intensity when the signal is fully recovered, and t is the $T_1$ recovery time. The person skilled in the art will readily determine the situations where one of the above listed pulse sequences could be beneficially used to extract reliable values of $T_1$.

The present inventors have thus disclosed a quality control technology using solvent NMR to determine if vaccines and other pharmaceutical products have been frozen and hence should be removed from the distribution stream because they may have a reduced potency and/or may be dangerous to a patient. The method described herein allows for the manufacturer and/or distributor and/or end user to monitor for freeze-induced damage during transport and/or storage. This can be done without opening the vial, i.e., non-invasively, or peeling off the label. Further advantages include the applicability of the method for both anti-bacterial and anti-viral vaccines, and any aqueous-based pharmaceutical products as defined herein.

As introduced herein, vaccines can be rendered thermally unstable when they are exposed to higher temperatures as well. Accordingly, in a third aspect, a method of determining if a vaccine or other aqueous-based pharmaceutical product has experienced heat-induced damage is described, said method comprising: measuring the relaxation rate of water $R_m$ in the vaccine or aqueous-based pharmaceutical product; and determining if the vaccine or aqueous-based pharmaceutical product has been heated by comparing the measured $R_m$ to a reference relaxation rate of water $R_r$, wherein the reference $R_r$ represents an acceptable range for non-heated vaccine or aqueous-based pharmaceutical product, wherein when the measured $R_m$ is inside the reference $R_r$ range, the vaccine or aqueous-based pharmaceutical product has not experienced heat-induced damage. In one embodiment, the pharmaceutical product comprises biologics or small molecules. In another embodiment, the vaccines or pharmaceutical products comprise at least one component selected from the group consisting of at least one adjuvant, at least one surfactant, at least one water-soluble organic solvent, at least one dispersant, at least one biocide, at least one buffering agent, at least one pH adjusting agent, at least one peptide, at least one polypeptide, at least one protein, at least one antibody or fragment thereof, at least one nucleic acid, at least one oil, and any combination thereof. The relaxation rate of water $R_1$ or $R_2$ can be determined using solvent NMR, preferably low field solvent NMR. Preferably, the measuring of the relaxation rate of water $R_1$ or $R_2$ in the vaccine or pharmaceutical product can be done non-invasively in a vial, but it should be appreciated that the measurement can be done invasively as well, as readily understood by the person skilled in the art. The reference $R_r$ range, at a specified temperature and magnetic field strength, can be measured by the manufacturer and the result listed in the package insert and/or the vial of the vaccine or pharmaceutical product. Preferably $R_m$ is measured at substantially the same temperature and magnetic field strength as $R_r$. The distributor or purchaser can then use NMR, e.g., benchtop or handheld, to measure $R_m$ at the specified temperature and magnetic field strength and compare it with the reference $R_r$ range listed in the package insert or vial before distribution or usage. If the measured $R_m$ is inside the reference $R_r$ range, the vaccine or aqueous-based pharmaceutical product has not experienced heat-induced damage, and as such can be distributed or used.

It should be appreciated that the method of the third aspect can be based on the water proton transverse relaxation time $T_2$, instead of the rate $R_2$, as readily determined by the person skilled in the art. In other words, when water is the solvent, the manufacturer provides $T_2(^1H_2O)$ reference values for the acceptable range for non-heat-induced damaged vaccine or aqueous-based pharmaceutical product and the measured $T_2(^1H_2O)$ of the vaccine or aqueous-based pharmaceutical product is compared to the $T_2(^1H_2O)$ reference values. Further, the method of the third aspect can be based on the water proton longitudinal relaxation time $T_1$, instead of the rate $R_1$, as readily determined by the person skilled in the art. In other words, when water is the solvent, the manufacturer provides $T_1(^1H_2O)$ reference values for the acceptable range for non-heat-induced damaged vaccine or aqueous-based pharmaceutical product and the measured $T_1(^1H_2O)$ of the vaccine or aqueous-based pharmaceutical product is compared to the $T_1(^1H_2O)$ reference values.

For the purposes of this disclosure, to have been rendered "thermally unstable" corresponds to a product having a $R_2(^1H_2O)$ or $R_1(^1H_2O)$ (or $T_2(^1H_2O)$ or $T_1(^1H_2O)$) value that is statistically different than the control that has not been rendered thermally unstable. For the purposes of this disclosure, "experienced heat-induced damage" is intended to mean that the storage temperature of the product has been increased, intentionally or accidentally, above a storage temperature designated as suitable for storage of the product. For example, for vaccines that are intended to be stored at refrigeration temperatures of about 2° C. to about 8° C., an increase in storage temperature above 8° C. may render the product thermally unstable. Similar to the freezing results discussed herein, it should be appreciated that just because the temperature of the vaccine or pharmaceutical product was for some period of time excursed above the refrigeration temperature for the specific product does not mean that the product has necessarily been rendered thermally unstable.

The features and advantages of the invention are more fully shown by the illustrative examples discussed below.

EXAMPLE 1

The transverse relaxation rate of the water proton NMR signal, $R_2(^1H_2O)$, of aluminum-containing vaccines exposed to a freeze-thaw cycle has been studied.

Vaccines Tested

Three different vaccines were tested. On each of these labels, it is specifically stated, "do not freeze. If product has been frozen, discard and do not use." Each vaccine has a different aluminum adjuvant, 0.5 mg Al(III) per dose/vial (0.5 mg/mL) for ENGERIX®-B (GlaxoSmithKline) as aluminum hydroxide, 0.33 mg Al(III) per dose/vial (0.66 mg/mL) for DAPTACEL® (Sanofi-Pasteur) as aluminum phosphate, and 0.45 mg Al(III) per dose/vial (0.45 mg/mL) for VAQTA® (Merck) as amorphous aluminum hydroxyphosphate sulfate. Each carton contained 10 vaccine vials and were labeled 1-10.

Storage and Measurement Procedures

Vaccines were stored according to their package insert instructions. All three vaccines required storage at 2-8° C. All vaccine cartons were stored in a 4° C. miniature refrigerator, located in the 18° C. room directly next to the benchtop NMR. The first four days of measurement, slight variations in the data were noticed, which were thought to be due to temperature variations due to the refrigerator cycling on and off as well as the refrigerator door opening and closing over the course of the measurements. Thereafter, the storage of the vials was adapted such that the cartons of vaccines were kept in temperature pre-equilibrated Styrofoam insulation boxes with lids, which were kept in the refrigerator. This helped to maintain a steady temperature of the vaccines throughout the course of measuring the 30 vials one at a time.

Figure 1:
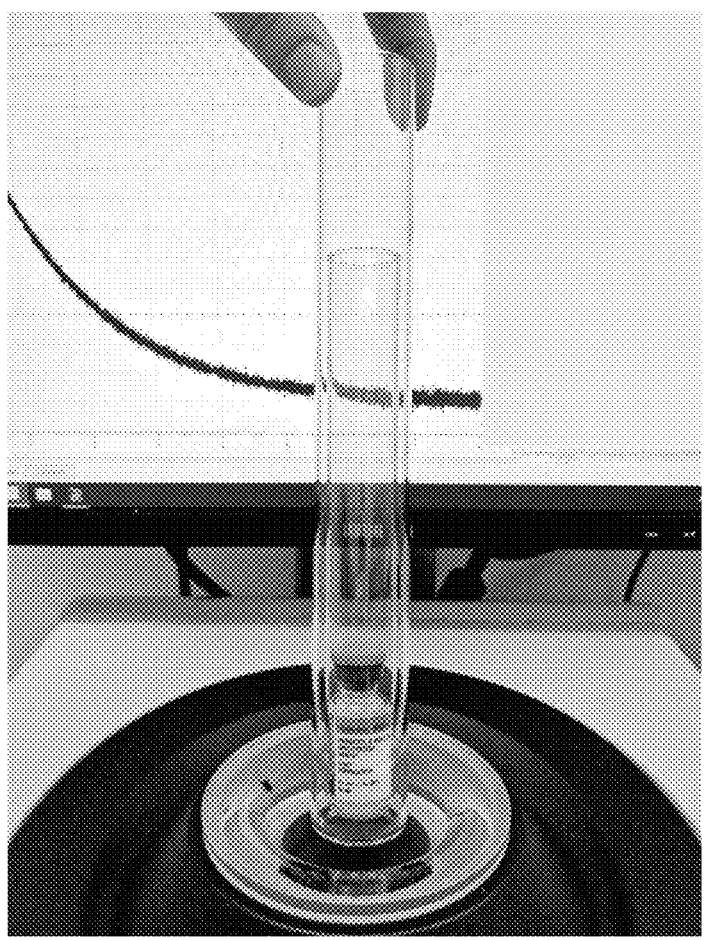
FIG. 1 is a photograph of a sealed unopened vial of the VAQTA vaccine drug product with label in two chilled (4° C.) NMR tubes as it is lowered the bore of the benchtop NMR.

The $R_2(^1H_2O)$ in $sec^{-1}$ of each vaccine vial was measured at 0.56 T (23.8 MHz $^1H$ resonance frequency, Oxford Instruments MQC+ equipped with a PRO 1193 probe) at approximately 4° C. To measure the transverse relaxation rate constant $R_2$, Carr-Purcell-Meiboom-Gill (CPMG) experiments were used. It should be appreciated by the person skilled in the art that there are other methods to determine $R_2$ and the use of CPMG in the examples described herein are not intended to limit the determination of $R_2$. Measurements of $R_2(^1H_2O)$ in $sec^{-1}$ were performed noninvasively, without opening the vial, since the wide bore (26 mm ID) of the probe of the low-field NMR spectrometer permitted the accommodation of the vial without drawing a portion of the sample and transferring it into standard NMR tube (FIG. 1).

The order in which the vials were measured within a box was rotated with every day of measurement to account for temperature differences throughout the course of the experiment as well as operator flow. Measurements were collected for three vials in a row followed by a six minute wait so that the glass NMR tubes could be re-cooled to 4° C.

It should be noted that the precautions disclosed herein were taken to ensure quality of measurement to show the efficacy of the method disclosed herein. It should be appreciated by the person skilled in the art that the precautions are merely illustrative and are not intended to limit the method of determining if a vaccine or aqueous-based pharmaceutical product has experienced freeze-induced damage in any way.

Freezing Procedure

Five of the ten vials of each vaccine product brand were frozen overnight for 17-22 hours (vials 6-10), while the other five (vials 1-5) were kept in the refrigerator at 4° C. as a control. The five vials that were frozen were exposed to freezing temperatures −17° C. to −19° C. followed by thawing at 4° C. for a total of three times. After each thawing, the $R_2(^1H_2O)$ was determined using a benchtop NMR for all ten vials, wherein vials 1-5 are the suspended, non-frozen control and vials 6-10 are the frozen vials. For the first freeze, vials 6-10 of the three vaccines (15 vials total) were set on the freezer floor, spaced at least two inches apart from each other and from anything else in the freezer. The three vaccines were then thawed in the refrigerator at 4° C. It was unexpected to have some vials of the same drug product not freeze while others froze. For the second freeze, the procedure was repeated except that this time all the vials to be frozen were shaken just as they were being placed in the freezer one by one. Additionally, to prevent any possible uneven freezing by touching the freezer floor, where there might be freeze coils beneath the floor, the vials were set on top of Styrofoam box lids. All the vials were spaced similarly to the first freezing. After each exposure to freezing temperatures and prior to thawing, visual observations of the physical state of the vaccine (solid frozen or liquid non-frozen) were written down. For the third freezing, all of the vials were unshaken/settled and had been undisturbed for 72 hours days prior to exposure to freezing temperatures.

Figure 2A:
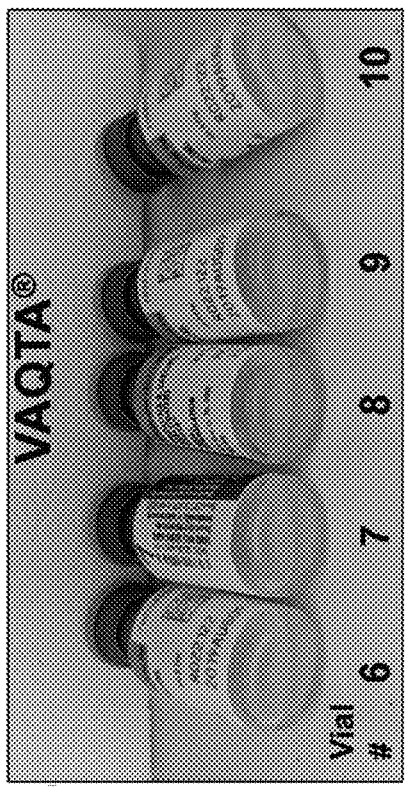
FIG. 2A is a photo of vials 6-10 of DAPTACEL after three exposures to −18° C., i.e., freezing temperatures, each for a duration of 17-22 hours, tilted on their sides to distinguish which vials froze because the labels obstruct the side view.
Figure 2B:
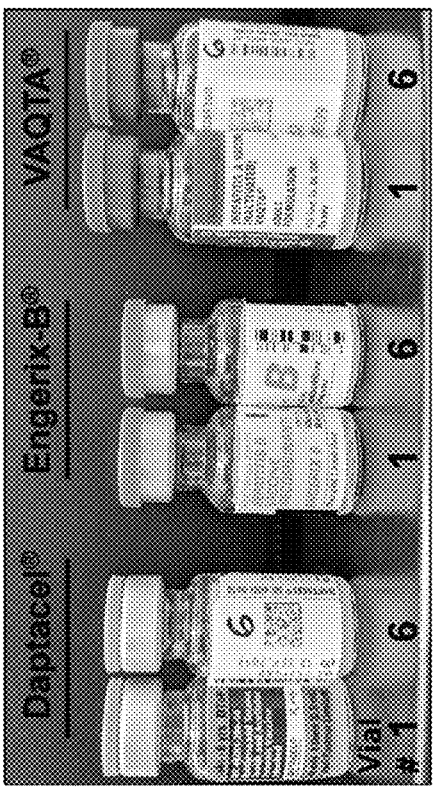
FIG. 2B is a photo of vials 6-10 of ENGERIX-B after three exposures to −18° C., i.e., freezing temperatures, each for a duration of 17-22 hours, tilted on their sides to distinguish which vials froze because the labels obstruct the side view.
Figure 2C:
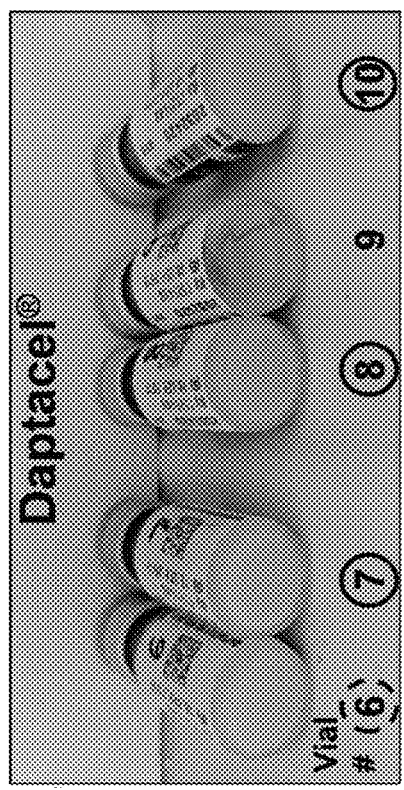
FIG. 2C is a photo of vials 6-10 of VAQTA after three exposures to −18° C., i.e., freezing temperatures, each for a duration of 17-22 hours, tilted on their sides to distinguish which vials froze because the labels obstruct the side view.
Figure 2D:
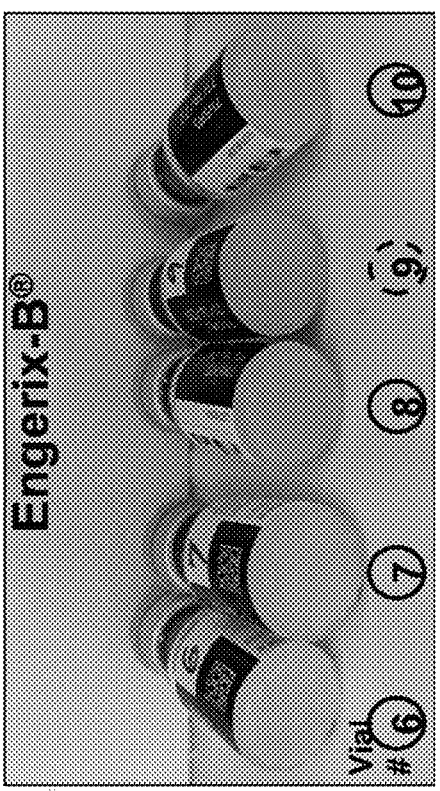
FIG. 2D shows the front label of vial 1 (unexposed to −18° C.) and the back label of vial 6 (exposed to −18° C.) of each vaccine, illustrating the difficulty distinguishing frozen and unfrozen visually without removing the label. Three vaccines (shown left to right) are: DAPTACEL (Sanofi-Pasteur, 0.5 mL), ENGERIX-B (GlaxoSmithKline, 1.0 mL), and VAQTA (Merck, 1.0 mL).

Photos of the three vaccines after three exposures to −18° C., i.e., freezing temperatures, are shown in FIG. 2, wherein FIG. 2A is DAPTACEL, FIG. 2B is ENERGIX-B, and FIG. 2C is VAQTA. All vials numbered 6-10 of each vaccine were exposed to −18° C. temperatures three separate times standing upright, each for a duration of 17-22 hours. They were tilted on their sides for the photos to distinguish which vials froze because the labels obstruct the side view. After the third exposure to freezing temperatures, it appeared that DAPTACEL #9 did not freeze (FIG. 2A), all of the ENGERIX-B vials froze (FIG. 2B), and none of the VAQTA vials froze (FIG. 2C). Vials were subsequently thawed at 4° C. for at least 1.5 hours prior to $R_2(^1H_2O)$ measurement at 4° C. Vial numbers are marked with a circle if they were frozen after the third exposure to −18° C. The circle is dashed if the vial did not freeze at either the first and/or second exposure to −18° C. Vials that did not freeze have no circle. FIG. 2D shows the front label of vial 1 (unexposed to −18° C.) and the back label of vial 6 (exposed to −18° C.), illustrating the difficulty distinguishing frozen and unfrozen visually without removing the label. Out of necessity, the WHO Shake Test often requires labels to be removed, for example because a children's single dose vaccine is a low volume, only 0.5 mL, which would make it difficult to observe visual differences otherwise.

Settled Product Measurements

All 30 vials were undisturbed for 1-2 weeks in a styrofoam 15 mL tube holder tray at 4° C. in order to let the suspension particles settle. For these NMR measurements, the same NMR procedure as the vaccine monitoring and freeze/thaw experiments were followed with a few changes to minimize any disturbances to the contents of the vials. For each experiment, the two chilled glass NMR tubes were placed one inside the other and lowered into the NMR bore. Means for clasping the vial necks were attached to each vial (e.g., a string tied into a lasso) and the vial was carefully placed at the mouth of the glass NMR tubes inside the instrument and carefully lowered into the tubes inside the benchtop NMR instrument. The $R_2(^1H_2O)$ was determined and the vials were then returned to the 4° C. environment.

Measurements of Vials Exposed to Freezing Conditions

Figures 3A, 3B, 3C:
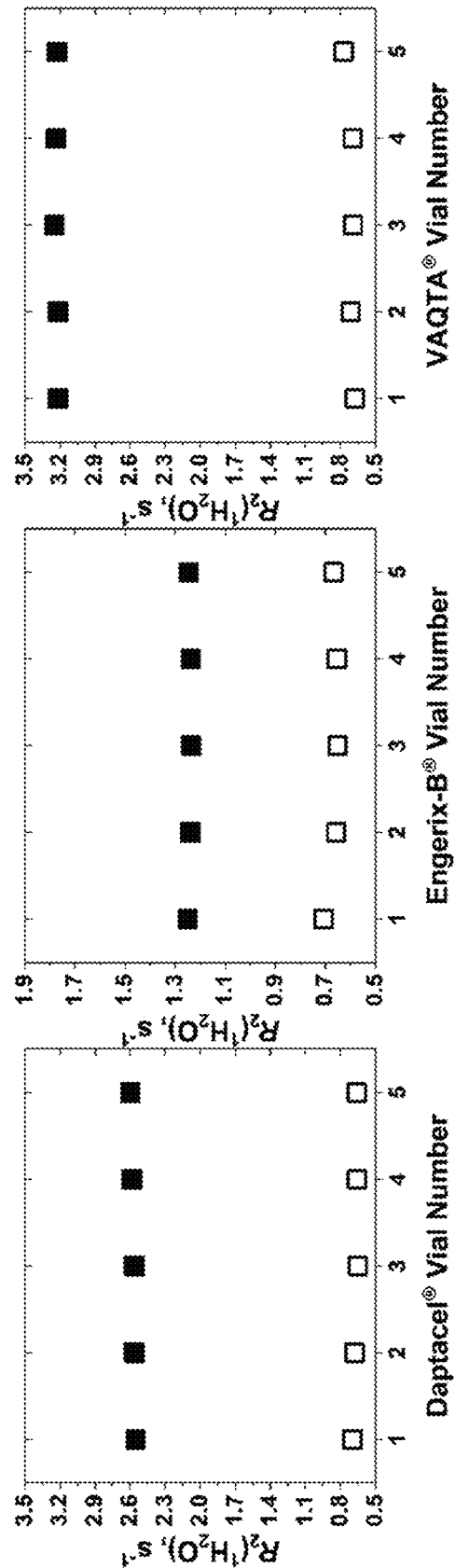
FIG. 3A illustrates the $R_2(^1H_2O)$ values for shaken and suspended vaccine vials 1-5 (solid squares) in contrast to $R_2(^1H_2O)$ values of fully settled/sedimented vaccine vials 1-5 (hollow square) for DAPTACEL. These vials were never exposed to freezing temperatures.
FIG. 3B illustrates the $R_2(^1H_2O)$ values for shaken and suspended vaccine vials 1-5 (solid squares) in contrast to $R_2(^1H_2O)$ values of fully settled/sedimented vaccine vials 1-5 (hollow square) for ENGERIX-B. These vials were never exposed to freezing temperatures.
FIG. 3C illustrates the $R_2(^1H_2O)$ values for shaken and suspended vaccine vials 1-5 (solid squares) in contrast to $R_2(^1H_2O)$ values of fully settled/sedimented vaccine vials 1-5 (hollow squares) for VAQTA. These vials were never exposed to freezing temperatures.

FIGS. 3A-3C illustrate the $R_2(^1H_2O)$ of shaken and suspended vaccine vials 1-5 (solid squares) shown in contrast to $R_2(^1H_2O)$ of fully settled/sedimented vaccine vials 1-5 (hollow square) for DAPTACEL (FIG. 3A), ENGERIX-B (FIG. 3B), and VAQTA (FIG. 3C). These vials were never exposed to freezing temperatures. The average $R_2(^1H_2O)$ for the control vials 1-5 (solid squares) from this third measurement, with standard deviation of 5 vials, was 2.541±0.016 s$^{-1}$ for DAPTACEL, 1.239±0.002 s$^{-1}$ for ENGERIX-B, and 3.238±0.011 s$^{-1}$ for VAQTA. The average $R_2(^1H_2O)$ of the settled vaccine vials 1-5 (hollow squares) with standard deviation of 3 measurements for each of the 5 vials, was 0.653±0.023 s$^{-1}$ for DAPTACEL, 0.687±0.026 s$^{-1}$ for ENGERIX-B, and 0.690±0.035 s$^{-1}$ for VAQTA.

Figures 4A, 4B, 4C:
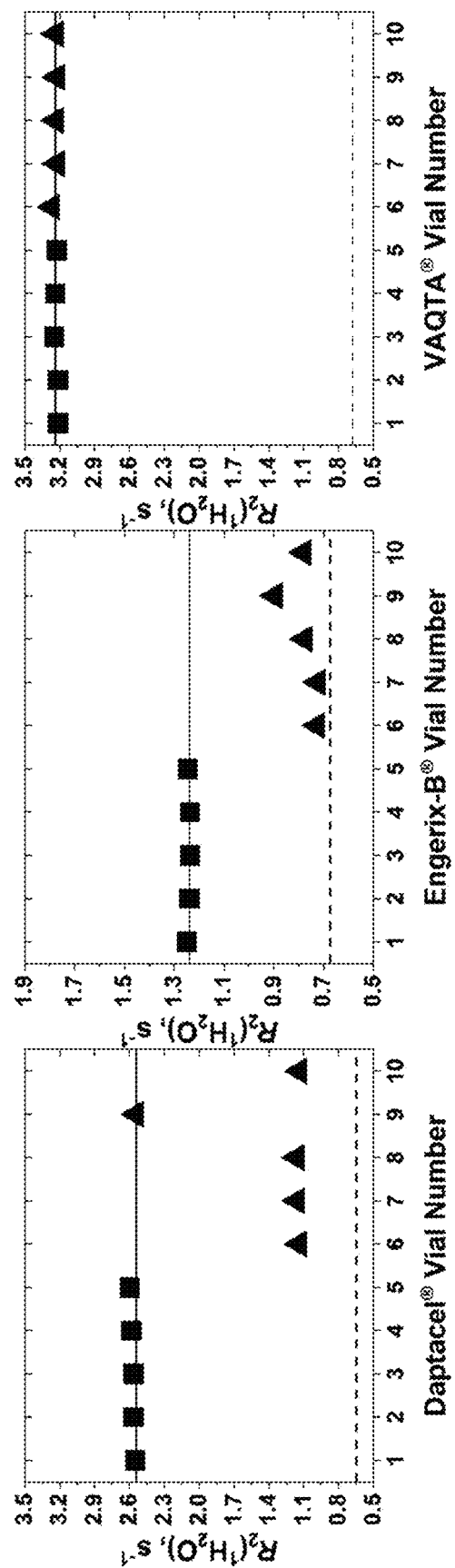
FIG. 4A illustrates the $R_2(^1H_2O)$ values of DAPTACEL vaccine suspensions vials 6-10 measured after the third exposure to freezing temperatures (−18° C.) overnight (17-22 hours) (black triangles) relative to unstressed vials 1-5 (black squares).
FIG. 4B illustrates the $R_2(^1H_2O)$ values of ENGERIX-B vaccine suspensions vials 6-10 measured after the third exposure to freezing temperatures (−18° C.) overnight (17-22 hours) (black triangles) relative to unstressed vials 1-5 (black squares).
FIG. 4C illustrates the $R_2(^1H_2O)$ values of VAQTA vaccine suspensions vials 6-10 measured after the third exposure to freezing temperatures (−18° C.) overnight (17-22 hours) (black triangles) relative to unstressed vials 1-5 (black squares).

$R_2(^1H_2O)$ of vaccine suspensions measured after the third exposure to freezing temperatures (−18° C.) are shown in FIG. 4A (DAPTACEL), FIG. 4B (ENGERIX-B), and FIG. 4C (VAQTA). Vials 6-10 (black triangles) were stressed, meaning they were exposed to −18° C. overnight (17-22 hours), subsequently brought to 4° C., and then the $R_2(^1H_2O)$ measured. This exposure to freezing temperatures and $R_2(^1H_2O)$ measurement cycle occurred three times. The data shown is from the third $R_2(^1H_2O)$ measurement. The data for the control vials 1-5 (non-frozen, solid line) from this third measurement, with standard deviation of 6 measurements, as well as the average $R_2(^1H_2O)$ for the settled vials (dashed lines) with standard deviation of 3 measurements for each of the 5 vials, are derived from the data presented in FIGS. 3A-3C and given in the previous paragraph.

Referring to FIG. 4A, it can be seen that the $R_2(^1H_2O)$ results verify that DAPTACEL vial 9 has approximately the same $R_2(^1H_2O)$ value as the non-frozen suspended vaccine, suggesting that DAPTACEL vial 9 did not experience any freeze-induced damage (compare to FIG. 2A). Referring to FIG. 4B, it can be inferred that every one of vials 6-10 of ENGERIX-B suffered freeze-induced damage since it is clear that the $R_2(^1H_2O)$ values are well below the average of the non-frozen suspended vaccine vials 1-5 (compare to FIG. 2B). Lastly, referring to FIG. 4C, it can be inferred that none of vials 6-10 of VAQTA suffered freeze-induced damage (compare to FIG. 2C).

Figures 5A, 5B:
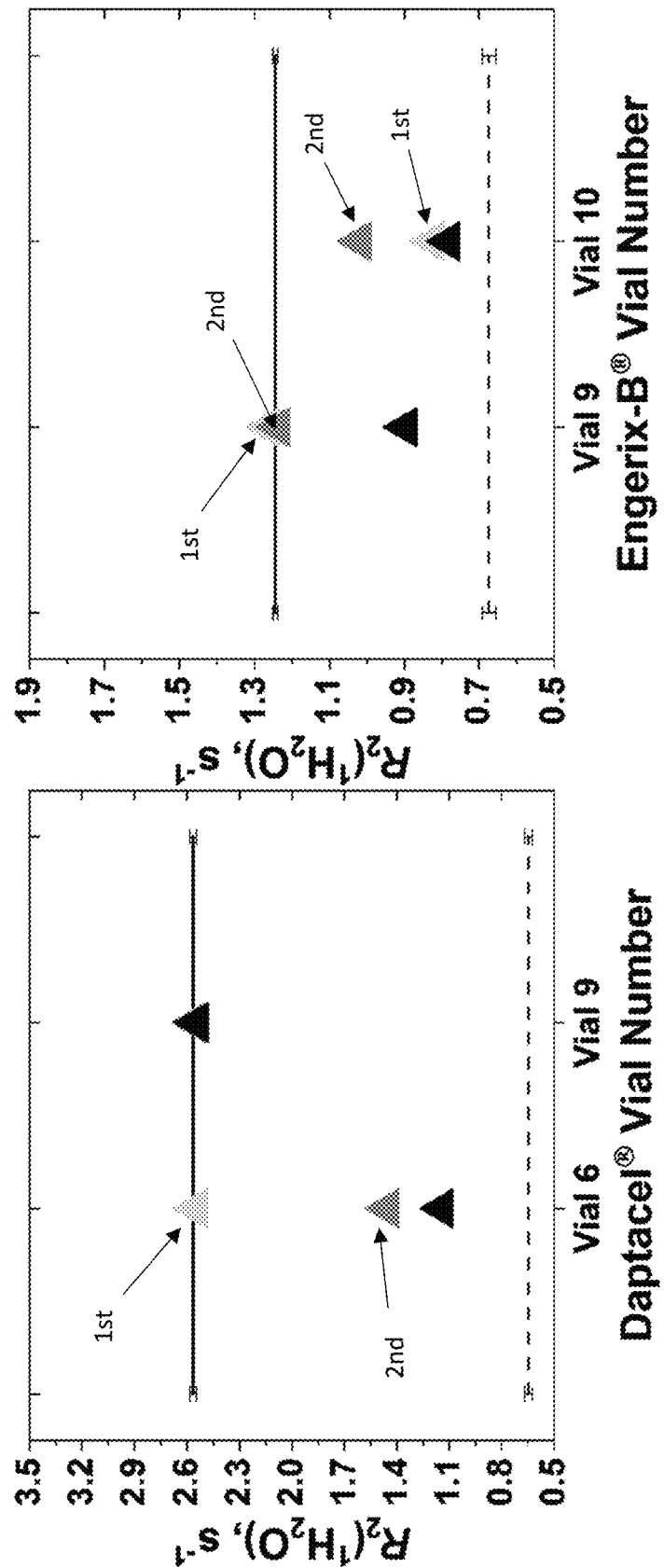
FIG. 5A illustrates the $R_2(^1H_2O)$ values of DAPTACEL vaccine vials 6 and 9 measured after the first exposure (light grey), second exposure (medium grey), and third exposure (black) to freezing temperatures (−18° C.). The upper solid line for DAPTACEL is the average $R_2(^1H_2O)$ of control vials 1-5 (unexposed to freezing temperatures) measured 3 times (2.566±0.020 s$^{-1}$). The lower dashed line is the 10-vial average of two settled $R_2(^1H_2O)$ measurements for each vaccine.
FIG. 5B illustrates the $R_2(^1H_2O)$ values of ENGERIX-B vaccine vials 9 and 10 measured after the first exposure (light grey), second exposure (medium grey), and third exposure (black) to freezing temperatures (−18° C.). The upper solid line for ENGERIX-B is the average $R_2(^1H_2O)$ of control vials 1-5 (unexposed to freezing temperatures) measured 3 times (1.245±0.006 s$^{-1}$). The lower dashed line is the 10-vial average of two settled $R_2(^1H_2O)$ measurements for each vaccine.

Interestingly, DAPTACEL vials 6 and 9, and ENGERIX-B vial 9 did not freeze initially upon first exposure to freezing temperatures (−18° C.) overnight (17-22 hours). Referring to FIGS. 5A and 5B, this physical observation after the first freezing (light grey) exposure was detectable noninvasively by $R_2(^1H_2O)$. The $R_2(^1H_2O)$ was also measured after the second exposure to freezing temperatures (medium grey) and third exposure (black). ENGERIX-B vial 9 did not freeze after second exposure, while DAPTACEL vial 6 froze. Finally, after the third exposure to freezing temperatures, both DAPTACEL vial 6 and ENGERIX-B Vial 9 were frozen. In contrast, DAPTACEL vial 9 did not freeze after the second or third exposure to freezing temperatures. ENGERIX-B vial 10 froze all three times, but exhibited a slightly different trend over the course of the three exposures to freezing temperatures. All $R_2(^1H_2O)$ measurements were of fully thawed, suspended vials at 4° C. FIGS. 5A and 5B highlight the non-uniform physical consequence of vaccine exposure to freezing temperatures (i.e., some vials froze, while others did not). The results of the vaccine suspensions exposed to freezing temperatures are easily compared to the average non-frozen suspended (solid line) and non-frozen settled (dashed line) results (corresponding to those shown in FIGS. 3A-3C).

Advantages of the Disclosed Method

Unexpectedly, some vials within the same carton experienced freeze-induced damage while others didn't (see, e.g., DAPTACEL vial 9 relative to vials 6-8 and 10). Further, some vaccines took multiple freeze-thaw cycles before freeze-induced damage was detected. Advantageously, the method described herein permits the user to easily determine, without having to destroy, alter or perturb the contents of the vial, whether each individual vial in a batch has experienced freeze-induced damage. This is a substantial improvement over the prior art, where one vial in a batch would be tested, for example using the WHO Shake Test, and if the vial showed evidence of freeze-induced damage, the entire batch was disposed of even if the rest of the batch had not experienced freeze-induced damage. At the same time, if the tested vial did not show evidence of freeze-induced damage, the entire batch would be distributed for use, which could be detrimental to the public if some of the vials in the batch had experienced freeze-induced damage. The results obtained for vials 6-10 DAPTACEL are an excellent example of why each vial is preferentially tested to determine if freeze-induced damage occurred, thus minimizing waste and maximizing potency. Using the method disclosed herein, the viability and potency of an entire batch of vaccines is no longer dependent on whether just one vial in the batch was determined to be frozen or non-frozen, e.g., using the "Shake Test" or knowing that the vaccines may have been exposed to freezing temperatures, but instead can be quickly determined by measuring the $R_2(^1H_2O)$ for each vial and comparing it to an acceptable $R_2(^1H_2O)$ value for the suspended batch.

Further, it is evident from the results in FIGS. 4B and 4C that some vaccines experience freeze-induced damage more easily than others. Both ENGERIX-B and VAQTA were exposed to the same freezing temperatures but only the ENGERIX-B experienced freeze-induced damage. The method described herein allows for the rapid and nondestructive determination of which of multiple different vaccines, exposed to the same temperatures, remain potent.

Overall, it can be concluded that the method described herein (wNMR) is a substantial improvement over the current state of the art, i.e., the Shake test or instrument-based sedimentation tests. wNMR is quantitative, and can be automated, removing the subjectivity of a highly trained human. wNMR can nondestructively test the vaccines and other pharmaceutical products without removing any labels, and regardless of the volume of product in the vial. The Shake test cannot be accurately performed on low volume vials, e.g., 0.5 mL and 1 mL. Advantageously, the acceptance decision regarding vaccines suspected of freezing based on wNMR is much more accurate. The use of wNMR can substantially ensure all injected vials have not been frozen and that all rejected vials have been frozen. This is because wNMR can be used to test every vial in a batch, unlike the Shake test which relies on the result from one vial in a batch to decide whether the entire batch should be injected or rejected. In other words, the results of the Shake test can potentially lead to situations where patients are injected with frozen vaccines or alternatively, where non-frozen vaccines have been disposed of. In addition, the wNMR method assesses the fully suspended product, without the necessity of a time course experiment, making the wNMR method very rapid, typically about 10-30 seconds. The Shake test and instrument-based sedimentation tests involve the monitoring of a time course as the product particles go from fully suspended to fully settled, which is very time consuming.

Measurement Controls

Vials of either ultrapure pure water or aluminum adjuvants served as negative and positive controls, respectively. Two commercially available aluminum adjuvants, ADJU-PHOS (the adjuvant in DAPTACEL) and ALHYDROGEL (the adjuvant in ENGERIX-B) were included as positive controls. The adjuvant in VAQTA is not commercially available and hence is not included. The freezing of pure water and two adjuvant suspensions served two purposes. One, they helped to determine whether the observed freezing variability was due to flawed freezing procedures or a faulty freezer, i.e., whether pure water or adjuvant suspensions display variable freezing behavior (some vials freeze, some do not). Second, they help to determine whether the observed $R_2(^1H_2O)$ decrease, in response to freeze/thaw, is a property of water alone, adjuvant in water, or the antigen-adjuvant complex in water.

Figure 6:
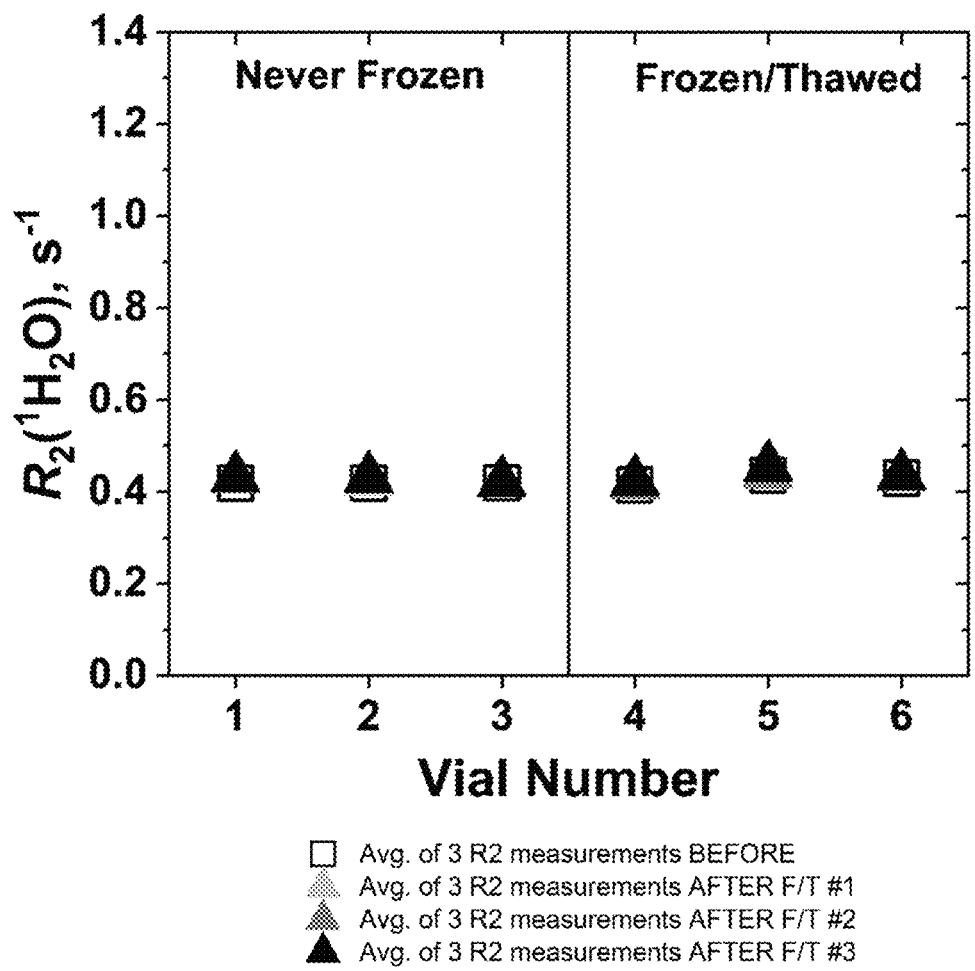
FIG. 6 illustrates the $R_2(^1H_2O)$ of frozen/thawed vials of ultrapure water is no different than control vials.

Six vials of pure water were prepared and the $R_2(^1H_2O)$ was measured prior to any freeze/thaw cycles to establish its baseline value. Vials 1-3 were kept at room temperature (23° C.). Vials 4-6 were exposed to subzero temperatures (−18° C.) overnight three times following the same freeze/thaw procedure as with the vaccine vials. The exposed vials 4-6 were visually observed to have frozen. However, unlike vaccine vials, for pure water, the $R_2(^1H_2O)$ of frozen/thawed vials is no different than control vials (FIG. 6). This result shows that the observed $R_2(^1H_2O)$ decrease of the vaccines in response to a freeze/thaw event is not due to the freezing of water.

Figure 7B:
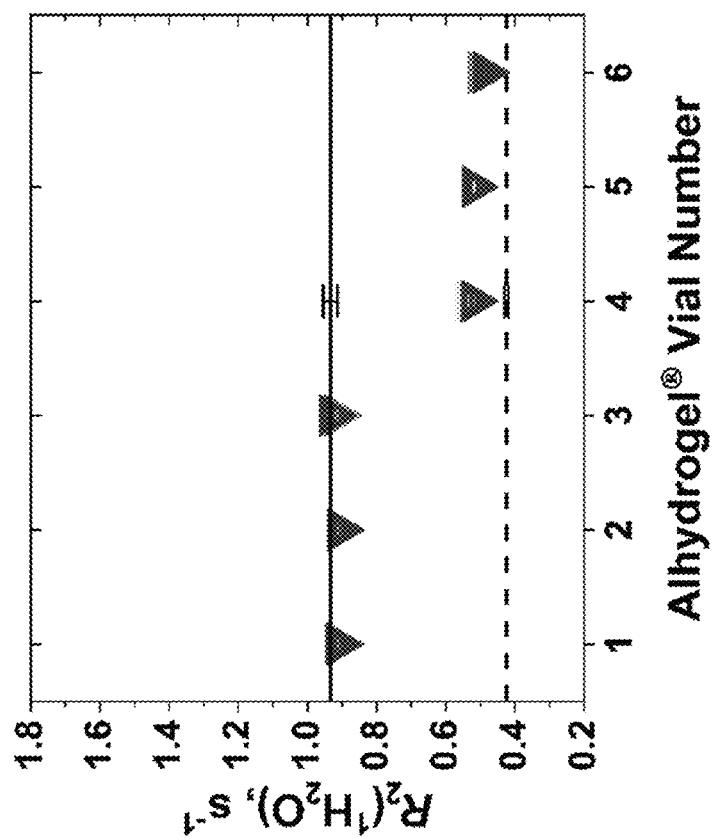
FIG. 7A illustrates $R_2(^1H_2O)$ of ADJUPHOS unstressed vials 1-3 and freeze/thaw vials 4-6 measured at 25° C. after the first (light triangle), second (medium triangle), and third (dark triangle) freeze-thaw cycle in the thawed liquid suspension state. Initial $R_2(^1H_2O)$ measurements of vials 1-6 (pre-freeze stress) are shown as averages in the suspended adjuvant (solid line) and settled adjuvant (dashed line) states.
Figure 7A:
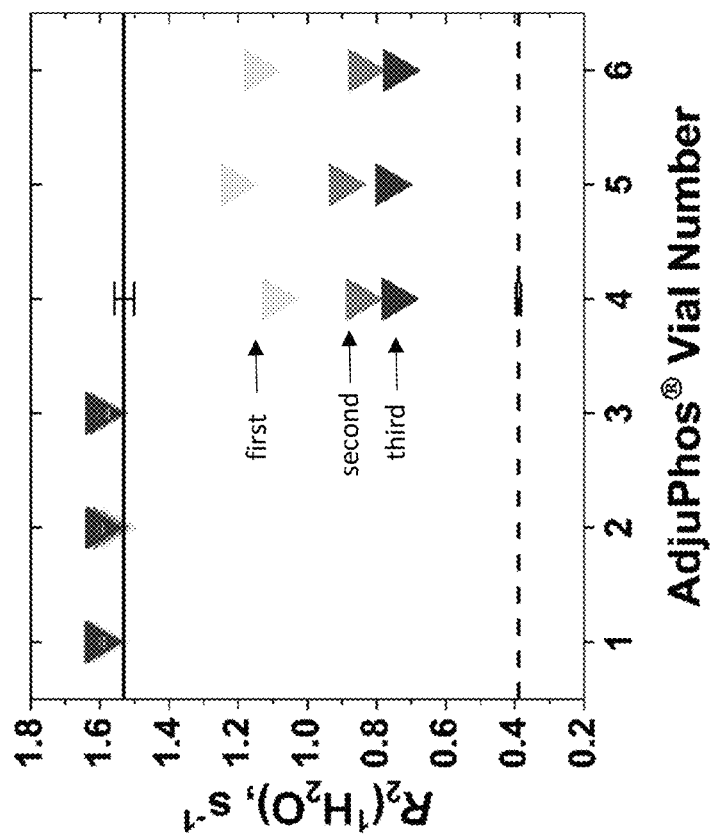

The next level assessed the aluminum adjuvant in water, without any antigens. Two suspensions were assessed, aluminum phosphate (ADJUPHOS, the adjuvant in DAPTACEL) and aluminum hydroxide (ALHYDROGEL, the adjuvant in ENGERIX-B), using the same freeze/thaw cycles as the vaccines. The aluminum concentration in the vials of ADJUPHOS was 0.66 mg/mL and in the vials of ALHYDROGEL was 0.50 mg/mL, matching the Al(III) in DAPTACEL and ENGERIX-B, respectively. Six vials of ADJUPHOS and six of ALHYDROGEL, each labeled 1-6, were measured initially to establish the high-quality adjuvant baseline in both suspended and settled states (FIG. 7). Vials 4-6 were then exposed to −18° C. for 19 hours. For both adjuvants, all the exposed vials were visually observed to have frozen. The frozen vials were then thawed at room temperature (23° C.) and the $R_2(^1H_2O)$ was measured. This process was repeated three times for both adjuvants.

Uniformity of freezing behavior was observed in the vials of water (FIG. 6) or aluminum adjuvant suspensions (FIG. 7). This uniformity in the freezing behavior of water and adjuvant vials demonstrates that the freezing procedure operation is not flawed, and the freezer is not faulty. The freeze/thaw of pure water led to no detectable changes in $R_2(^1H_2O)$, while the freeze/thaw of aluminum adjuvant led to a significantly lower $R_2(^1H_2O)$. Further, ADJUPHOS displayed a larger decrease in $R_2(^1H_2O)$ than ALHYDROGEL (0.86 vs 0.40 $s^{-1}$), consistent with DAPTACEL displaying a larger $R_2(^1H_2O)$ decrease than ENGERIX-B (0.61 vs 0.17 $s^{-1}$). This suggests that the observed $R_2(^1H_2O)$ decrease in response to freeze/thaw events emerges at the adjuvant in water level. In vaccines, the magnitude of this decrease may be modulated by antigens and/or excipients.

EXAMPLE 2

The transverse relaxation rate of the water proton NMR signal, $R_2(^1H_2O)$, of PROPOFOL and DIPRIVAN exposed to a freeze-thaw cycle has been studied. PROPOFOL is the generic product of the brand name DIPRIVAN. They are injectable emulsions indicated for general anesthesia and sedation that are administered intravenously. The package inserts of both products state "Do not freeze," rendering them freeze-sensitive products.

One vial of each product (DIPRIVAN and PROPOFOL) was opened and the contents (20 mL whitish emulsion) were aliquoted into six glass vials (3 mL/vial). The reason for opening the vial is because the 20-mL vial (o.d. 30 mm) cannot fit into the benchtop NMR that was available (limit: 26 mm) It should be appreciated by the person skilled in the art that had the NMR magnet bore been greater than the outside diameter of the vial, the vial could have been inserted directly into the NMR without opening the vial (i.e., a non-invasive measurement). Just before aliquoting, the product was inverted several times for uniform dispersion of emulsion. The six glass vials of each product were labelled 1-6 and were measured using wNMR. Following initial measurements, vials 1-3 of each product were stored at room temperature (i.e., unstressed), while vials 4-6 were subjected to overnight freezing at −30° C. in a pre-equilibrated Bio-Cool instrument for approximately 17 hours and then thawed at room temperature (i.e., stressed). Again, vials 1-6 for each product were measured using wNMR.

DIPRIVAN and PROPOFOL do not require cold storage and hence the NMR measurement was made at 25° C., which is the temperature of the benchtop NMR magnet. Three consecutive measurements were collected of each vial.

As seen from FIG. 8A, visual detection of the freezing history of the emulsion drugs is not possible. Unstressed and stressed (previously frozen) vials look very similar if not identical. FIG. 8B illustrates the average of vials 1-3 and vials 4-6, where 0 F/T refers to vials 1-3 with no freeze thaw, and 1 F/T refers to vials 4-6, which were frozen at −30° C. and subsequently thawed prior to the measurement. It can be seen in FIG. 8B that the $R_2(^1H_2O)$ for both products increased by approximately 0.065 sec$^{-1}$ after one freeze/thaw cycle. Accordingly, water proton relaxation rate $R_2(^1H_2O)$ readily detects the difference between stressed and unstressed products and allows the user to easily identify a pharmaceutical product with a freezing history.

EXAMPLE 3

An unopened vial of DIPRIVAN (10 mL) was stored at room temperature (~25° C.), according to storage requirements detailed in the package insert. The $T_2(^1H_2O)$ of this vial was measured 12 times, as described herein, once on 12 different non-consecutive days. $R_2(^1H_2O)$ was calculated from the $T_2(^1H_2O)$, as understood by the person skilled in the art. Referring to FIG. 9B, the average $R_2(^1H_2O)$ for unopened DIPRIVAN having zero freeze-thaws ("0 F/T") is 0.509±0.010 s$^{-1}$, with an error bar showing the standard deviation of the 12 measurements (i.e. the measurement variability). The vial was subsequently exposed to −30° C. overnight (16+ hours) and frozen, then thawed and equilibrated to 25° C. The $T_2(^1H_2O)$ was measured, and the $R_2(^1H_2O)$ was determined to be 0.564 s$^{-1}$ (labeled "1 F/T" in FIG. 9B, for one freeze-thaw). The magnitude of $R_2(^1H_2O)$ change is 0.055 s$^{-1}$, well above the measurement error of 0.010 This result shows that $R_2(^1H_2O)$ can readily detect the one F/T cycle experienced by unopened DIPRIVAN.

In comparison, when the vial is opened, $R_2(^1H_2O)$ of DIPRIVAN increased from 0.549±0.0003 s$^{-1}$ (from an average of 3 vials, each measured 3 times) before freezing to 0.612±0.0003 s$^{-1}$ (from an average of 3 vials, each measured 3 times) after one F/T cycle. The magnitude of $R_2(^1H_2O)$ change is 0.063 s$^{-1}$. The percentage of change (calculated by the magnitude of change in $R_2(^1H_2O)$ before and after freezing divided by the $R_2(^1H_2O)$ before freezing) for unopened DIPRIVAN and opened DIPRIVAN are both 11%.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

1. Pasquale, A., S. Preiss, F. Silva, and N. Garçon. 2015. Vaccine Adjuvants: from 1920 to 2015 and Beyond. Vaccines. 3: 320-343.
2. Gupta, R. K., and E. R. Bradford Relyveld, Edgar, and Siber, George R. 1995. Adjuvant Properties of Aluminum and Calcium Compounds. In: Powell M F, M J Newman, editors. Vaccine Design: The Subunit and Adjuvant Approach. New York, NY: Plenum Press. pp. 229-248.
3. Hem, S. L., and J. L. White. 1995. Structure and Properties of Aluminum-Containing Adjuvants. In: Powell M F, M J Newman, editors. Vaccine Design: The Subunit and Adjuvant Approach. New York, NY: Plenum Press. pp. 249-276.
4. Baylor, N. W., W. Egan, and P. Richman. 2002. Aluminum salts in vaccines—US perspective. Alum. Adjuv. Vaccines Work. Summ 20: S18-S23.
5. Kumru, O. S., S. B. Joshi, D. E. Smith, C. R. Middaugh, T. Prusik, and D. B. Volkin. 2014. Vaccine instability in the cold chain: Mechanisms, analysis and formulation strategies. Biologicals. 42: 237-259.
6. Dumpa, N., K. Goel, Y. Guo, H. McFall, A. R. Pillai, A. Shukla, M. A. Repka, and S. N. Murthy. 2019. Stability of Vaccines. AAPS PharmSciTech. 20: 42.
7. Kurzątkowski, W., Ü. Kartoğlu, M. Staniszewska, P. Górska, A. Krause, and M. J. Wysocki. 2013. Structural damages in adsorbed vaccines affected by freezing. Biologicals. 41: 71-76.
8. Chesko, J., T. Vedvick, and S. Reed. 2013. Novel immune potentiators and delivery technologies for next generation vaccines. Nov. Immune Potentiators Deliv. Technol. Next Gener. Vaccines.: 1-369.
9. Østergaard, E., P. L. Frandsen, and E. Sandberg. 2015. Determination of freeze damage on HPV vaccines by use of flow cytometry. Biologicals. 43: 266-273.
10. Metz, B., G. van den Dobbelsteen, C. van Els, J. van der Gun, L. Levels, L. van der Pol, N. Rots, and G. Kersten. 2009. Quality-control issues and approaches in vaccine development. Expert Rev. Vaccines. 8: 227-238.
11. Clapp, T., M. W. Munks, R. Trivedi, U. B. Kompella, and L. J. Braun. 2014. Freeze-thaw stress of Alhydrogel® alone is sufficient to reduce the immunogenicity of a recombinant hepatitis B vaccine containing native antigen. Vaccine. 32: 3765-3771.
12. World Health Organization 2006, WHO/IVB/06.10.
13. Lloyd, J., and J. Cheyne. 2017. The origins of the vaccine cold chain and a glimpse of the future. Vaccine. 35: 2115-2120.
14. Robertson, J., L. Franzel, and D. Maire. 2017. Innovations in cold chain equipment for immunization supply chains Vaccine. 35: 2252-2259.
15. World Health Organization 2005, WHO/V&B/03.18.Rev.1.
16. Setia, S., H. Mainzer, M. L. Washington, G. Coil, R. Snyder, and B. G. Weniger. 2002. Vaccine. 20: 1148-1156.
17. CDC. 2019. Centers for Disease Control and Prevention Guidelines for Vaccine Storage and Handling U S Dep. Heal. Hum. Serv.: 1-49.
18. World Health Organization. 2015. Module 2: The Vaccine Cold Chain Immun Pract. A Pract. Guid. Heal. Staff.: 44-46.
19. 2010. How to perform the "Shake Test." XXXII: 2010.
20. Clausi, A. L., S. A. Merkley, J. F. Carpenter, and T. W. Randolph. 2008. Inhibition of aggregation of aluminum hydroxide adjuvant during freezing and drying. J. Pharm. Sci. 97: 2049-2061.
21. Wolff, L., J. Flemming, R. Schmitz, K. Gröger, and C. Müller-Goymann 2008. Protection of aluminum hydroxide during lyophilisation as an adjuvant for freeze-dried vaccines. Colloids Surfaces A Physicochem. Eng. Asp. 330: 116-126.
22. Dimayuga R., D. Scheifele, and A. Bell. 1995. Effects of freezing on DTP and DTP-IPV vaccines, adsorbed. Can. Commun Dis. Rep. 21: 101-3 pmid: 7647743.
23. Kartoglu U., N. K. Özgüler, L. J. Wolfson, and W. Kurzatkowski. 2010. Validation of the shake test for detecting freeze damage to adsorbed vaccines. Bulletin of the World Health Organization. 88:624-631.
24. Metz, H., K. Mäder. 2008. Benchtop-NMR and MRI—a new analytical tool in drug delivery research. Int. J. Pharm. 364: 170-178.

What is claimed is:

1. A method of determining if a vaccine or aqueous-based pharmaceutical product has experienced freeze-induced damage, wherein the vaccine or aqueous-based pharmaceutical product comprises an aluminum adjuvant, said method comprising:
measuring a transverse relaxation rate of solvent $R_{2,m}$ in the vaccine or the aqueous-based pharmaceutical product; and
determining if the vaccine or the aqueous-based pharmaceutical product has been frozen by comparing the measured $R_{2,m}$ to a reference transverse relaxation rate of solvent $R_{2,r}$ for the respective vaccine or aqueous-based pharmaceutical product, wherein the reference $R_{2,r}$ represents an acceptable range for non-frozen vaccine or non-frozen aqueous-based pharmaceutical product,
wherein when the measured $R_{2,m}$ of the vaccine or aqueous-based pharmaceutical product is less than the reference $R_{2,r}$ range, the vaccine or aqueous-based pharmaceutical product has not experienced freeze-induced damage, and wherein the vaccine or aqueous-based pharmaceutical product is contained in a vial, and wherein no additives or probes are added to the vial prior to measurement of the transverse relaxation rate of solvent $R_{2,m}$.

2. The method of claim 1, wherein the aqueous-based pharmaceutical product comprises biologics or small molecules.

3. The method of claim 1, wherein the vaccine or aqueous-based pharmaceutical product further comprises at least one component selected from the group consisting of at least one surfactant, at least one water-soluble organic solvent, at least one dispersant, at least one biocide, at least one buffering agent, at least one pH adjusting agent, at least one peptide, at least one polypeptide, at least one protein, at least one antibody or fragment thereof, at least one nucleic acid, at least one oil, and any combination thereof.

4. The method of claim 1, wherein the aluminum adjuvant comprises an aluminum-containing salt selected from the group consisting of aluminum hydroxide, aluminum phosphate, aluminum sulfoxyphosphate, aluminum hydroxyphosphate sulfate, alum ($KAl(SO_4) \cdot 12H_2O$), and any combination thereof.

5. The method of claim 1, wherein the $R_{2,m}$ is measured using nuclear magnetic resonance (NMR).

6. The method of claim 5, wherein $R_{2,m}$ and $R_{2,r}$ are measured at a substantially similar magnetic field strength.

7. The method of claim 1, wherein the $R_{2,m}$ is measured without opening the vial or otherwise accessing contents of the vial.

8. The method of claim 1, wherein the solvent is water.

9. The method of claim 1, wherein the vaccine or aqueous-based pharmaceutical product that has experienced freeze-induced damage is not used or distributed as intended.

10. The method of claim 1, wherein $R_{2,m}$ and $R_{2,r}$ are measured at a substantially similar temperature.

11. The method of claim 10, comprising the vaccine, wherein the temperature is in a range from about 2° C. to about 8° C.

12. The method of claim 1, wherein the aqueous-based pharmaceutical product comprises an emulsion.

13. A method of determining if a vaccine or aqueous-based pharmaceutical product has experienced freeze-induced damage, wherein the vaccine or aqueous-based pharmaceutical product comprises an aluminum adjuvant, said method comprising:
measuring a transverse relaxation time of solvent $T_{2,m}$ in the vaccine or aqueous-based pharmaceutical product; and
determining if the vaccine or the aqueous-based pharmaceutical product has been frozen by comparing the measured $T_{2,m}$ to a reference transverse relaxation time of solvent $T_{2,r}$ for the respective vaccine or aqueous-based pharmaceutical product, wherein the reference $T_{2,r}$ represents an acceptable range for non-frozen vaccine or non-frozen aqueous-based pharmaceutical product,
wherein when the measured $T_{2,m}$ of the vaccine or aqueous-based pharmaceutical product is less than the reference $T_{2,r}$ range, the vaccine or aqueous-based pharmaceutical product has experienced freeze-induced damage, and wherein the vaccine or aqueous-based pharmaceutical product is contained in a vial, and wherein no additives or probes are added to the vial prior to measurement of the transverse relaxation time of solvent $T_{2,m}$.

14. The method of claim 13, wherein the $T_{2,m}$ is measured using nuclear magnetic resonance (NMR).

15. The method of claim 13, wherein the $T_{2,m}$ is measured without opening the vial or otherwise accessing contents of the vial.

16. The method of claim 13, wherein the solvent is water.

17. The method of claim 13, wherein the aqueous-based pharmaceutical product comprises biologics or small molecules.

18. The method of claim 13, wherein $T_{2,m}$ and $T_{2,r}$ are measured at a substantially similar temperature.

19. The method of claim 13, wherein the vaccine or aqueous-based pharmaceutical product further comprises at least one component selected from the group consisting of at least one surfactant, at least one water-soluble organic solvent, at least one dispersant, at least one biocide, at least one buffering agent, at least one pH adjusting agent, at least one peptide, at least one polypeptide, at least one protein, at least one antibody or fragment thereof, at least one nucleic acid, at least one oil, and any combination thereof.

20. The method of claim 13, wherein the aluminum adjuvant comprises an aluminum-containing salt selected from the group consisting of aluminum hydroxide, aluminum phosphate, aluminum sulfoxyphosphate, aluminum hydroxyphosphate sulfate, alum ($KAl(SO_4) \cdot 12H_2O$), and any combination thereof.

* * * * *